(12) United States Patent
Shashar et al.

(10) Patent No.: US 12,369,946 B2
(45) Date of Patent: Jul. 29, 2025

(54) DELAYING PRE-TERM BIRTH

(71) Applicant: PregnanTech Ltd., D.N. Misgav (IL)

(72) Inventors: David Shashar, Shoham (IL); Shahar Harari, Tel-Aviv (IL); Nir Lilach, Kfar Yehoshua (IL); Eliahu Eliachar, Haifa (IL); Assaf Agou, Haifa (IL); Dotan Tromer, Moshav Hosen (IL); Yosef Hazan, Haifa (IL)

(73) Assignee: PregnanTech Ltd., D.N. Misgav (IL)

( * ) Notice: Subject to any disclaimer, the term of this patent is extended or adjusted under 35 U.S.C. 154(b) by 662 days.

(21) Appl. No.: 17/254,334

(22) PCT Filed: Jun. 20, 2019

(86) PCT No.: PCT/IL2019/050696
§ 371 (c)(1),
(2) Date: Dec. 21, 2020

(87) PCT Pub. No.: WO2019/244159
PCT Pub. Date: Dec. 26, 2019

(65) Prior Publication Data
US 2021/0236170 A1    Aug. 5, 2021

Related U.S. Application Data

(60) Provisional application No. 62/846,831, filed on May 13, 2019, provisional application No. 62/687,841, filed on Jun. 21, 2018.

(51) Int. Cl.
*A61B 17/42* (2006.01)
*A61B 17/00* (2006.01)
*A61B 17/12* (2006.01)

(52) U.S. Cl.
CPC .... *A61B 17/42* (2013.01); *A61B 2017/00893* (2013.01); *A61B 2017/12018* (2013.01); *A61B 2017/4225* (2013.01)

(58) Field of Classification Search
CPC ........ A61B 17/42; A61B 2017/00893; A61B 2017/12018; A61B 2017/4225;
(Continued)

(56) References Cited

U.S. PATENT DOCUMENTS

| 604,958 A | 5/1898 | Biesmeyer |
| 804,086 A | 11/1905 | Barchfeld et al. |

(Continued)

FOREIGN PATENT DOCUMENTS

| CN | 202365885 | 8/2012 |
| CN | 202458542 | 10/2012 |

(Continued)

OTHER PUBLICATIONS

Examination Report Under Sections 12 & 13 of the Patents Act, 1970 and the Patents Rules, 2003 Dated Oct. 11, 2022 From the Government of India, Intellectual Property India, Patents, Designs, Trade Marks, Geographical Indications, The Patent Office Re. Application No. 202127002499. (6 Pages).

(Continued)

*Primary Examiner* — Brooke Labranche

(57) ABSTRACT

A device for retarding birth, forming a lumen for surrounding a uterine cervix, the device including an upper ring for surrounding the uterine cervix, and an anchoring mechanism for anchoring the device on the cervix. A tool for inserting a device for retarding birth, the device including a device lumen for surrounding a uterine cervix, the tool including a plurality of rods attached to two rings, forming a longitudinal tool lumen, each rod including a connector for attaching to the device for retarding birth at a distal end of the rod, and a mechanism at a proximal end of the rod, for detaching the device for retarding birth at the distal end of the rod. Related apparatus and methods are also described.

26 Claims, 32 Drawing Sheets

(58) Field of Classification Search
CPC .............. A61B 17/0482; A61B 17/29; A61B 2017/00858; A61B 2017/0472; A61B 2017/2902; A61B 2017/2912; A61B 2017/2932; A61B 2017/2946; A61B 5/435; A61B 5/4356; A61B 17/0469; A61B 17/12009; A61B 1/303; A61B 17/12013; A61B 17/4241; A61B 17/44; A61F 6/08; A61F 6/12
See application file for complete search history.

(56) References Cited

U.S. PATENT DOCUMENTS

| | | | |
|---|---|---|---|
| 1,019,373 | A | 3/1912 | Shaulis |
| 1,083,721 | A | 1/1914 | Asch |
| 1,162,568 | A | 11/1915 | Carey |
| 1,219,496 | A | 3/1917 | Shaulis |
| 1,634,555 | A | 7/1927 | Peloubet |
| 2,618,261 | A | 11/1952 | Butts |
| 3,741,216 | A | 6/1973 | Yosowitz et al. |
| 5,807,281 | A | 9/1998 | Welch |
| 5,871,499 | A | 2/1999 | Hahn |
| 6,981,990 | B2 | 1/2006 | Keller |
| 8,550,088 | B1 | 10/2013 | Booher, Sr. |
| 2004/0092847 | A1 | 5/2004 | Welch |
| 2004/0153008 | A1 | 8/2004 | Sharf et al. |
| 2004/0236349 | A1 | 11/2004 | Gellman |
| 2008/0171950 | A1 | 7/2008 | Franco |
| 2010/0043802 | A1 | 2/2010 | O'Brien |
| 2010/0228269 | A1 | 9/2010 | Garrison et al. |
| 2011/0307011 | A1 | 12/2011 | Moskowitz |
| 2013/0053670 | A1 | 2/2013 | Aina-Mumuney et al. |
| 2013/0231704 | A1 | 9/2013 | Larroque-Lahiltette |
| 2013/0237766 | A1 | 9/2013 | Pell et al. |
| 2014/0073879 | A1 | 3/2014 | Cantor et al. |
| 2014/0276916 | A1 | 9/2014 | Ahluwalia et al. |
| 2015/0216472 | A1 | 8/2015 | Aina-Mumuney et al. |
| 2016/0361169 | A1* | 12/2016 | Gross .................... A61F 2/2445 |
| 2017/0020529 | A1* | 1/2017 | Tsur ...................... A61M 31/00 |
| 2017/0087344 | A1* | 3/2017 | Ichim .................. A61M 31/002 |
| 2019/0008674 | A1 | 1/2019 | Myers et al. |
| 2019/0183530 | A1* | 6/2019 | Yang ................ A61B 17/12009 |
| 2020/0129179 | A1 | 4/2020 | Tsur et al. |
| 2023/0329723 | A1 | 10/2023 | Tsur et al. |

FOREIGN PATENT DOCUMENTS

| | | | |
|---|---|---|---|
| CN | 106794029 | | 5/2017 |
| EP | 0084755 | | 12/1982 |
| FR | 2455881 | | 12/1980 |
| JP | H10-118048 | | 5/1998 |
| TW | 106144244 | * 12/2017 | ....... A61B 17/12009 |
| TW | 201927265 | | 7/2019 |
| WO | WO 85/00008 | | 1/1985 |
| WO | WO 01/01899 | | 1/2001 |
| WO | WO 2010/021695 | | 2/2010 |
| WO | WO 2010/114577 | | 10/2010 |
| WO | WO 2011/103473 | | 11/2011 |
| WO | WO 2014/164700 | | 10/2014 |
| WO | WO 2015/159291 | | 10/2015 |
| WO | WO 2019/244159 | | 12/2019 |
| WO | WO 2019/244159 A8 | | 2/2020 |
| WO | WO 2019/244159 A9 | | 2/2021 |

OTHER PUBLICATIONS

Communication Pursuant to Article 94(3) EPC Dated May 12, 2023 From the European Patent Office Re. Application No. 15780710.8 (10 Pages).
Supplementary Partial European Search Report and the Provisional Opinion Dated Feb. 15, 2022 From the European Patent Office Re. Application No. 19822823.1. (20 Pages).
Notice of Allowance Mar. 15, 2023 from the US Patent and Trademark Office Re. U.S. Appl. No. 16/706,986. (8 pages).
Official Action Dated Oct. 18, 2022 From the US Patent and Trademark Office Re. U.S. Appl. No. 16/706,986. (29 Pages).
Communication Pursuant to Article 94(3) EPC Dated Feb. 18, 2020 From the European Patent Office Re. Application No. 15780710.8. (12 Pages).
Communication Relating to the Results of the Partial International Search Dated Jul. 28, 2015 From the International Searching Authority Re. Application No. PCT/IL2015/050402.
European Search Report and the European Search Opinion Dated Nov. 15, 2017 From the European Patent Office Re. Application No. 15780710.8. (12 Pages).
International Preliminary Report on Patentability Dated Oct. 27, 2016 From the International Bureau of WIPO Re. Application No. PCT/IL2015/050402. (9 Pages).
International Preliminary Report on Patentability Dated Dec. 30, 2020 From the International Bureau of WIPO Re. Application No. PCT/IL2019/050696. (12 Pages).
International Search Report and the Written Opinion Dated Sep. 1, 2015 From the International Searching Authority Re. Application No. PCT/IL2015/050402.
International Search Report and the Written Opinion Dated Nov. 14, 2019 From the International Searching Authority Re. Application No. PCT/IL2019/050696. (42 Pages).
Invitation to Pay Additional Fees and Communication Relating to the Results of the Partial International Search Dated Sep. 26, 2019 From the International Searching Authority Re. Application No. PCT/IL2019/050696. (26 Pages).
Notice Of Allowance Dated Jul. 31, 2019 From the US Patent and Trademark Office Re. Application No. 15/30,190. (10 pages).
Notice of Reason for Rejection Dated Mar. 5, 2019 From the Japan Patent Office Re. Application No. 2014-513308 and Its Translation Into English. (12 Pages).
Notification of Office Action and Search Report Dated Jun. 5, 2019 From the State Intellectual Property Office of the People's Republic of China Re. Application No. 201580031813.X. (5 Pages).
Notification of Office Action Dated Sep. 4, 2018 From the State Intellectual Property Office of the People's Republic of China Re. Application No. 201580031813.X and Its Translation Into English. (4 Pages).
Official Action Dated Feb. 7, 2019 From the US Patent and Trademark Office Re. U.S. Appl. No. 15/302,190. (15 pages).
Restriction Official Action Dated Aug. 8, 2018 From the US Patent and Trademark Office Re. U.S. Appl. No. 15/302,190. (7 pages).
Translation of Notification Dated Jun. 18, 2019 From OA of Jun. 5, 2019 From the State Intellectual Property Office of the People's Republic of China Re. Application No. 201580031813.X. (2 Pages).
ACOG "Cerclage for the Management of Cervical Insufficiency", The American College of Obstetricians and Gynecologists, Clinical Management Guidelines for Obstetrician-Gynecologists, Practice Bulletin 142, 123(2 Pt.1): 372-379, Feb. 2014.
ACOG "The Management of Preterm Labor", The American College of Obstetricians and Gynecologists, Clinical Management Guidelines for Obstetrician- Gynecologists, Practice Bulletin 127, 119(6): 1308-1317, Jun. 2012.
Lawn et al. "Global Report on Preterm Birth and Stillbirth (1 of 7): Definitions, Description of the Burden and Opportunities to Improve Data", BMC Pregnancy and Childbirth, 10(Suppl.1): S1-S22, 2010.
Verma et al. "Continuous Wireless Monitoring of the Cervical Dilation of a Pregnant Woman", IEEE International Workshop on Medical Measurements and Applications: 1-4, May 9-10, 2008.
Restriction Official Action Dated Mar. 2, 2022 from US Patent and Trademark Office Re. U.S. Appl. No. 16/706,986. (5 pages).
Supplementary European Search Report and the European Search Opinion Dated May 17, 2022 From the European Patent Office Re. Application No. 19822823.1. (13 Pages).
Examination Report Under Sections 12 & 13 of the Patents Act, 1970 and the Patents Rules, 2003 Dated Jan. 22 From the Government of India, Intellectual Property India, Patents, Designs, Trade Marks, Geographical Indications, The Patent Office Re. Application No. 201627035298. (5 Pages).
Relatório de Busca e Parecer [Search Report and Opinion] Dated May 23, 2023 From the Serviço Público Federal, Ministério da

(56) References Cited

OTHER PUBLICATIONS

Economia, Instituto Nacional da Propriedade Industrial do Brasil Re. Application No. BR 11 2020 026131 9 and Its Translation Into English. (7 Pages).
English Summary Dated Jan. 10, 2024 of Notification of Office Action Dated Dec. 28, 2023 From the National Intellectual Property Administration of the People's Republic of China Re. Application No. 201980052404.6. (3 Pages).
Machine Translation Dated Jan. 7, 2023 of Notification of Office Action Dated Dec. 28, 2023 From the National Intellectual Property Administration of the People's Republic of China Re. Application No. 201980052404.6. (11 Pages).
Notification of Office Action and Search Report Dated Dec. 28, 2023 From the National Intellectual Property Administration of the People's Republic of China Rc. Application No. 201980052404.6. (10 Pages).
Communication Pursuant to Article 94(3) EPC Dated Nov. 8, 2023 From the European Patent Office Re. Application No. 19822823.1 (5 Pages).
Hearing Notice Dated Nov. 30, 2023 From the Government of India, Intellectual Property India, The Patent Office Re. Application No. 201627035298. (2 Pages).
Restriction Official Action Dated Nov. 19, 2024 from US Patent and Trademark Office Re. U.S. Appl. No. 18/212,790. (7 pages).
Relatorio de Exame Tecnico [Technical Examination Report] Dated Dec. 31, 2024 From the Servico Publico Federal, Ministerio da Economia, Instituto Nacional da Propriedade Industrial do Brasil Re. Application No. BR 11 2020 026131 9 and Its Translation into English. (8 Pages).
Notification of Office Action and Search Report Dated Aug. 9, 2024 From the State Intellectual Property Office of the People's Republic of China Re. Application No. 201980052404.6 and Its Machine Translation Into English. (16 Pages).
Relatório de Exame Tecnico Dated Mar. 6, 2025 From the Serviço Público Federal, Ministério da Economia, Instituto Nacional da Propriedade Industrial do Brasil Re. Application No. BR 11 2020 026131 9 and Its Translation Into English. (10 Pages).

* cited by examiner

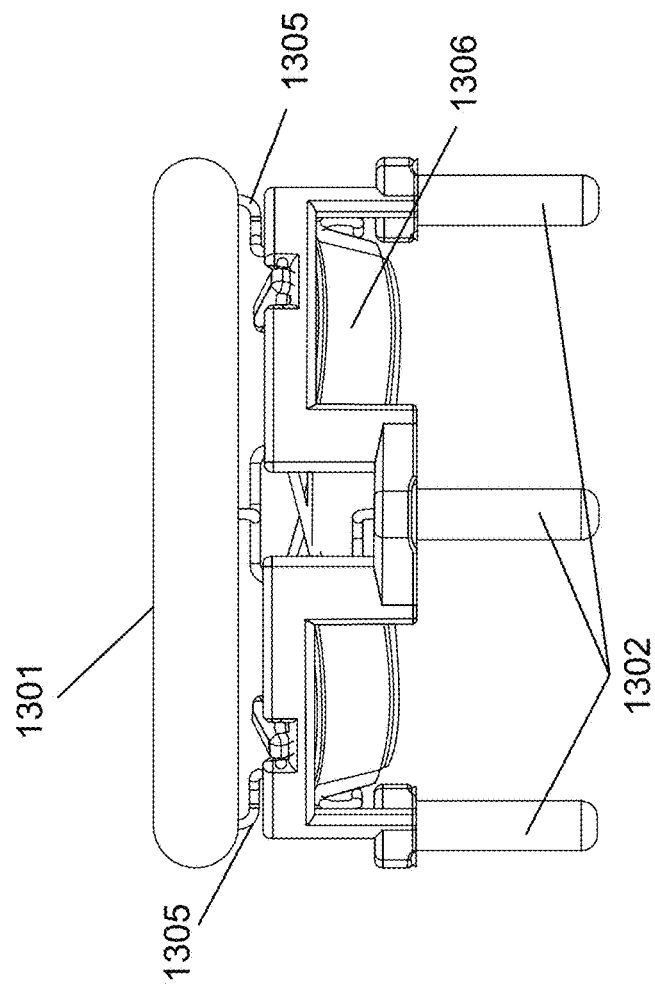
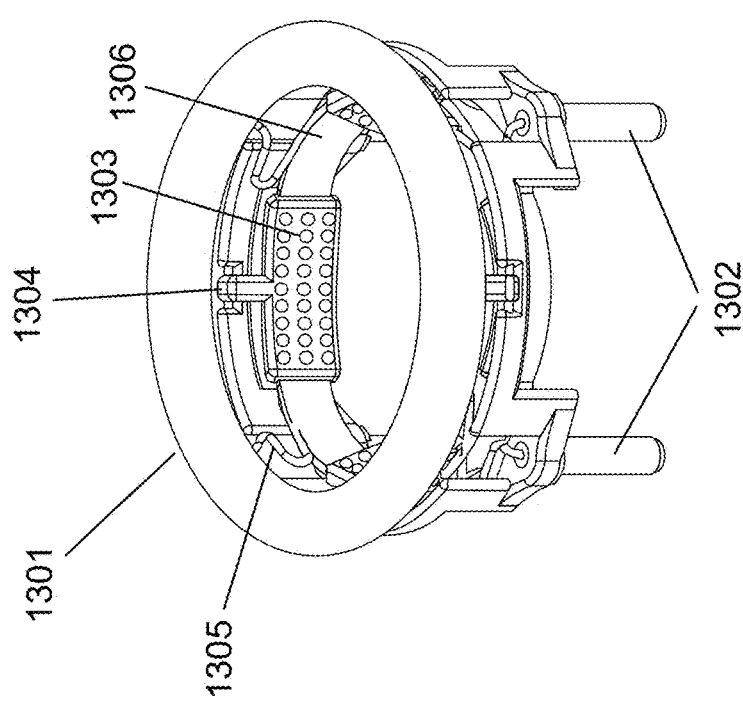
FIG. 13A
FIG. 13B

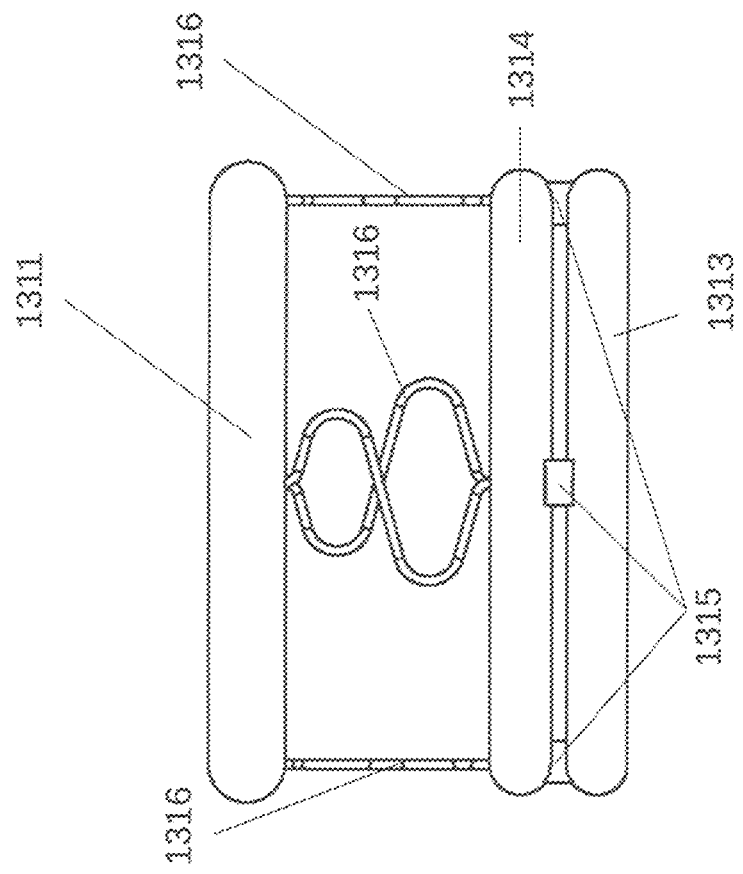
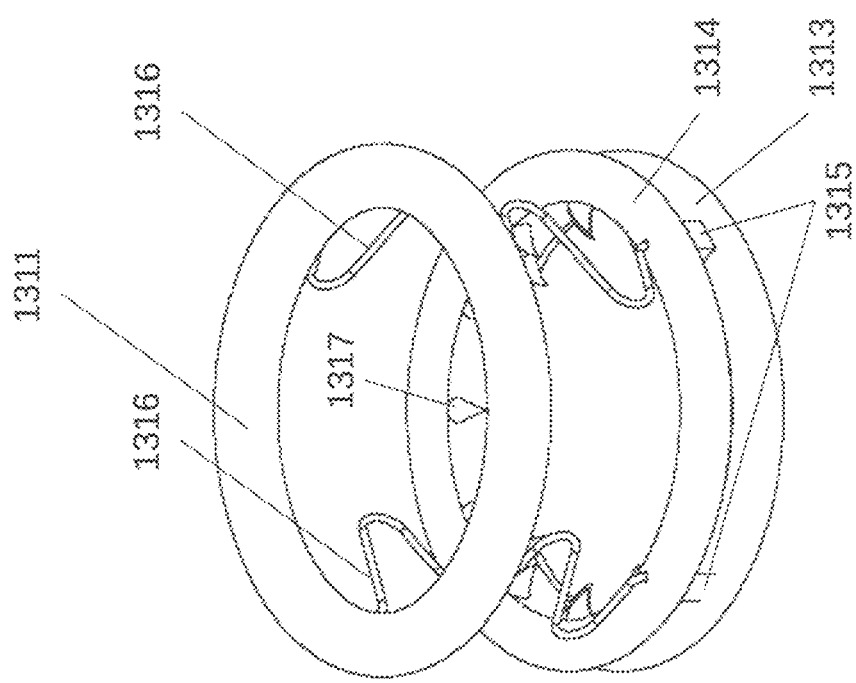
FIG. 13D
FIG. 13C

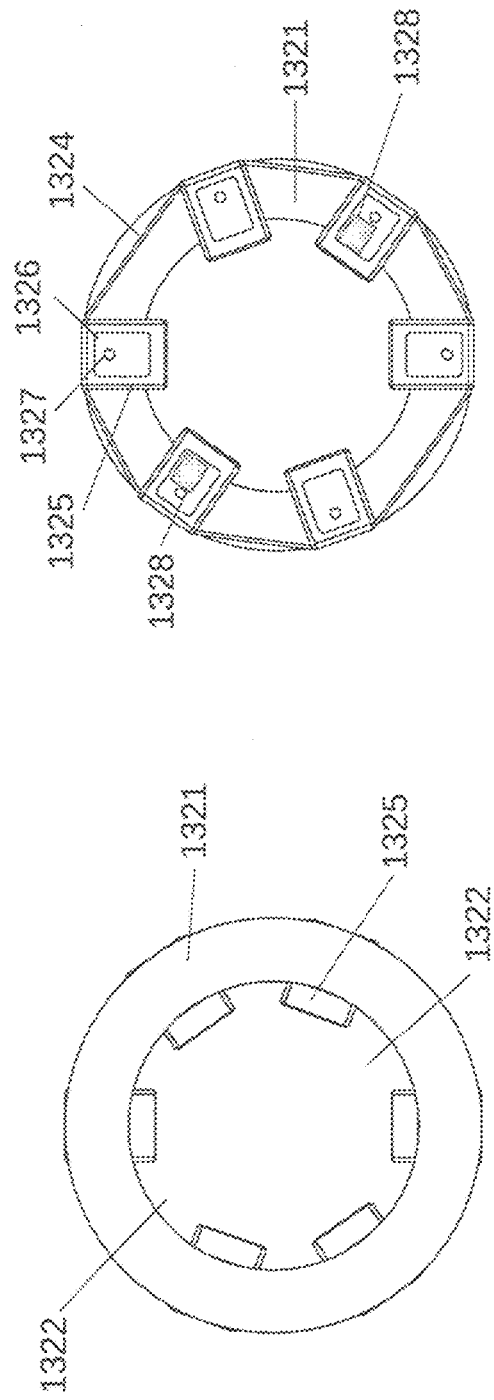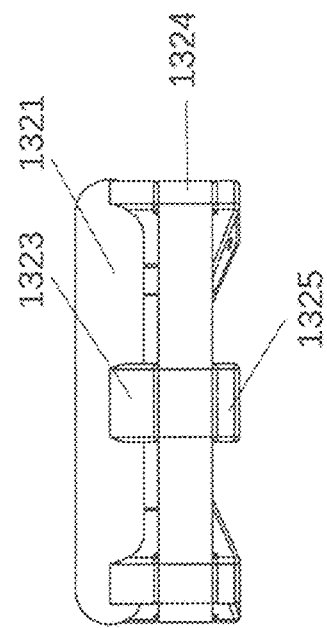

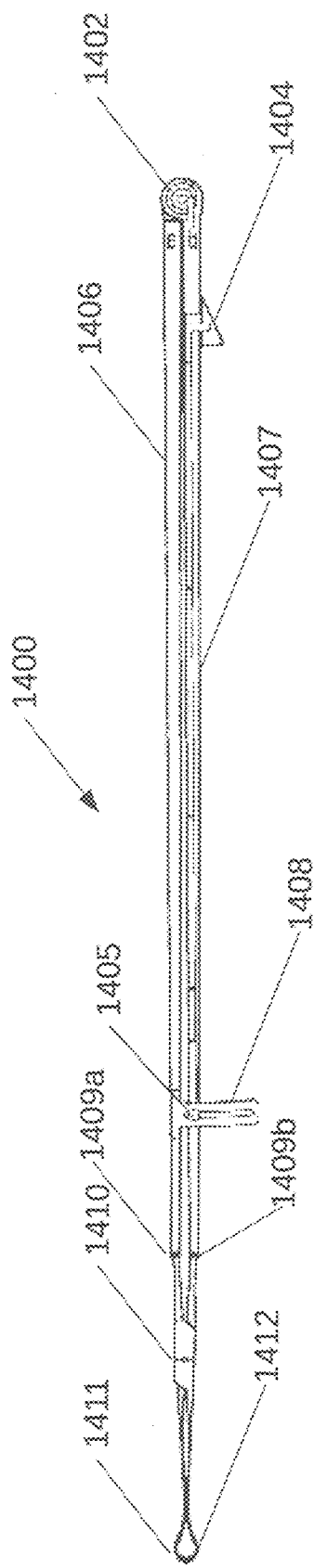
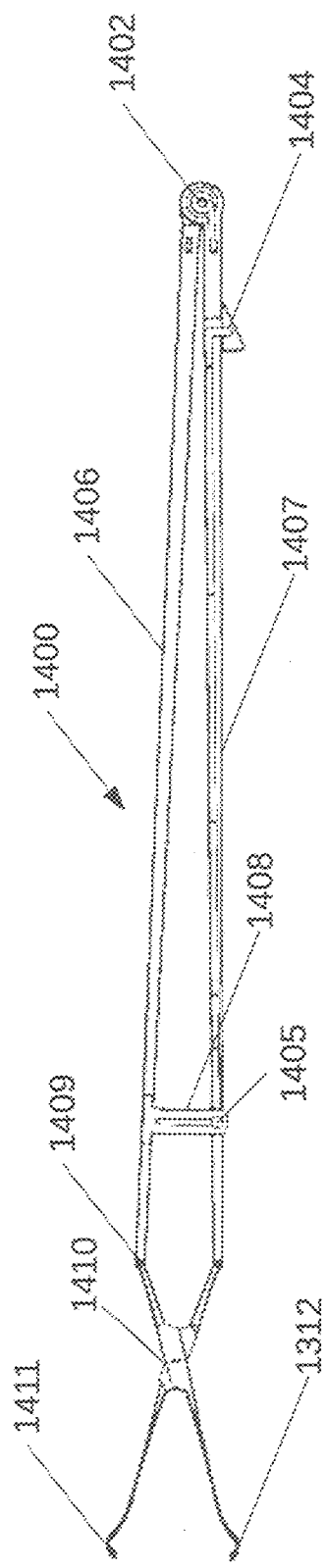
FIG. 14A
FIG. 14B

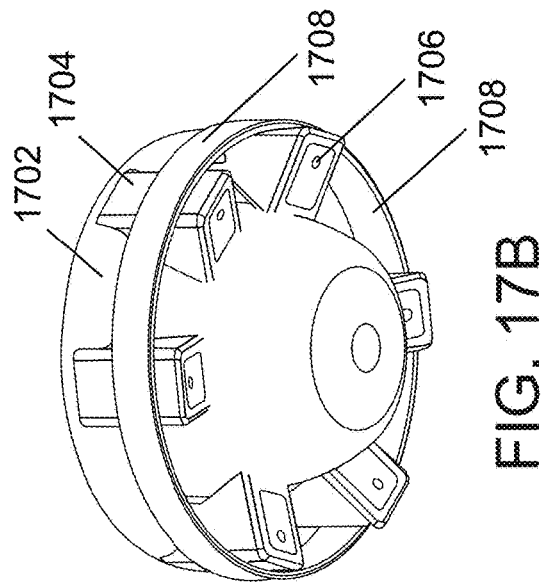
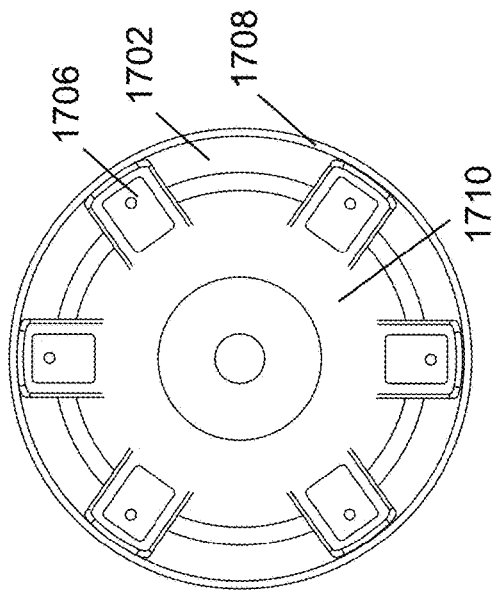
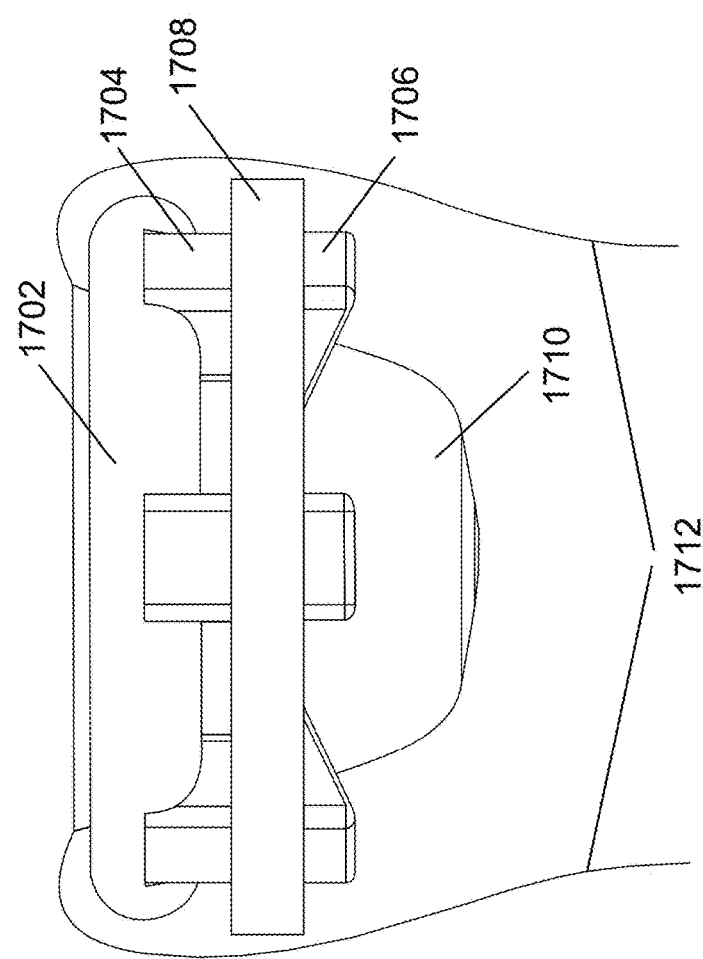

DELAYING PRE-TERM BIRTH

RELATED APPLICATIONS

This application is a National Phase of PCT Patent Application No. PCT/IL2019/050696 having International filing date of Jun. 20, 2019 which claims the benefit of priority under 35 USC § 119(e) of U.S. Provisional Patent Application Nos. 62/687,841 filed on Jun. 21, 2018 and 62/846,831 filed on May 13, 2019. The contents of the above applications are all incorporated by reference as if fully set forth herein in their entirety.

FIELD AND BACKGROUND OF THE INVENTION

The present invention, in some embodiments thereof, relates to devices and methods for delaying pre-term birth or pre-term delivery and, more particularly, but not exclusively, to devices inserted into the vagina and surrounding the cervix and to related methods.

Preterm birth (delivery at 24 to 37 weeks of pregnancy) is the leading cause of newborn death and illness. Worldwide 15M babies a year are born preterm. 1M will die and 1M will suffer from substantial life-long complications: breathing disorders, feeding disorders or neural disabilities—blindness, hearing loss, neurodevelopment delay or cerebral palsy. Babies born prematurely pose a huge financial burden to society. In the US, costs associated with preterm birth surpass $26B annually.

Major risks of spontaneous pre-term labor causing approximately 50% of pre-term births are previous preterm birth, twin pregnancies or multiple pregnancies, cervical shortening, cervical insufficiency, uterine premature contractions (PMC) or a combination of these.

Treatments such as medications and hormones, stitching the cervix (cerclage) and pessaries are often unsatisfactory in reducing the rate of spontaneous preterm birth.

The disclosures of all references throughout the present specification, as well as the disclosures of all references mentioned in those references, are hereby incorporated herein by reference.

SUMMARY OF THE INVENTION

An aspect of some embodiments of the invention relates to inserting a device into a vagina for safely supporting the cervix, preventing progression of cervical dilatation, effacement or funneling and preventing or delaying preterm labor.

According to an aspect of some embodiments of the present invention there is provided a device for retarding birth, forming a lumen for surrounding a uterine cervix, the device including an upper ring for surrounding the uterine cervix, and an anchoring mechanism for anchoring the device on the cervix.

According to some embodiments of the invention, further including a band surrounding the anchoring mechanism.

According to some embodiments of the invention, the anchoring mechanism includes a plurality of anchoring components.

According to some embodiments of the invention, the anchoring mechanism includes a needle. According to some embodiments of the invention, the anchoring mechanism includes a suturing needle. According to some embodiments of the invention, a shape of the needle maybe selected from: straight; ¼circle; ⅜ circle; ½ circle; ⅝ circle; compound curve; half curved (also known as ski); and half curved at both ends of a straight segment (also known as canoe).

According to some embodiments of the invention, further including a mechanism for extending the needle from a surface of the anchoring mechanism.

According to some embodiments of the invention, further including a spring for extending the needle from a surface of the anchoring mechanism.

According to some embodiments of the invention, the upper ring is elastic.

According to some embodiments of the invention, the upper ring includes a spring.

According to some embodiments of the invention, the anchoring components include a protrusion toward an inside of the lumen the protrusion designed to resist movement of the anchoring component along tissue.

According to some embodiments of the invention, the anchoring components include an adhesive material directed toward an inside of the lumen designed to resist movement of the anchoring component along tissue.

According to some embodiments of the invention, the anchoring components include a sharp needle.

According to some embodiments of the invention, the anchoring components include a plurality of sharp needles.

According to some embodiments of the invention, the band includes an elastic ring surrounding the anchoring mechanism.

According to some embodiments of the invention, the anchoring component includes a foot having a protrusion toward a cervix side, the protrusion having a shape selected from a group consisting of a single rectangular protrusion toward a cervix side, a spherical protrusion toward the cervix side, two rectangular protrusions toward the cervix side, and a hemispherical protrusion with the round side of the hemisphere toward the cervix side or other shapes which act to anchor against the cervix.

The term foot is used herein to mean a radial extension from the device for retarding birth radially inward toward a center axis of the device.

In some embodiments the foot is attached to a lower portion of a leg of the device, the term leg being used as defined elsewhere herein.

According to some embodiments of the invention, the anchoring component includes at least one pin toward a cervix side.

According to some embodiments of the invention, at least some of the anchoring components include a hole for suturing the device to the uterine cervix.

According to some embodiments of the invention, the anchoring components are distributed equi-distantly around the lumen.

According to some embodiments of the invention, the anchoring components are distributed non-equi-distantly around the lumen.

According to some embodiments of the invention, the number of anchoring components is an even number in a range from two to twenty inclusive.

According to some embodiments of the invention, the number of anchoring components is an uneven number in a range from three to twenty one inclusive.

According to some embodiments of the invention, further including a component for measuring data from a group consisting of contractions, dilatation of a cervix, and progress of labor.

According to some embodiments of the invention, further including a component for gathering data from a group consisting of contractions, dilatation of a cervix, and progress of labor.

According to some embodiments of the invention, further including a component for eluting a drug.

According to some embodiments of the invention, further including a component for gathering data regarding preterm birth.

According to some embodiments of the invention, further including a component for gathering data regarding pregnancy at term.

According to some embodiments of the invention, further including a component for gathering data regarding a condition of a fetus.

According to some embodiments of the invention, further including a vibrating mechanism for relief and relaxation.

According to an aspect of some embodiments of the present invention there is provided a method for retarding birth including providing a device for retarding birth which forms a lumen for surrounding a uterine cervix, inserting the device into a vagina such that the lumen surrounds the uterine cervix, locating the device such that the upper ring surrounds the cervix in a fornix and in proximity to a level of the cervical internal os, and placing the device such that the device grips the uterine cervix.

According to some embodiments of the invention, the device comprises an upper ring for surrounding the uterine cervix and an anchoring mechanism for anchoring the device on the cervix.

According to some embodiments of the invention, the inserting includes compressing the device to pass through a vaginal introitus.

According to some embodiments of the invention, the inserting includes compressing the device to pass through a vaginal introitus.

According to some embodiments of the invention the inserting includes twisting the device to pass through a vaginal introitus.

According to some embodiments of the invention the inserting includes inserting the device to pass through a speculum situated in the vagina.

According to some embodiments of the invention, the locating of the device such that the upper ring surrounds the cervix includes releasing compression of the device to assist the device to surround the cervix.

According to some embodiments of the invention, the locating of the device such that the upper ring surrounds the cervix includes expanding the device to assist the device to surround the cervix. In some embodiments the upper ring is expanded in order to push the upper ring up along the cervix.

According to some embodiments of the invention, the placing of the device such that the upper ring surrounds the cervix includes releasing the expanding of the device.

According to some embodiments of the invention, the device further includes a band surrounding the device, and further including removing the band from around the device.

According to some embodiments of the invention, further including extracting the band from a patient's body.

According to some embodiments of the invention, the device grips the uterine cervix by pressing on the uterine cervix.

According to some embodiments of the invention, the device anchors to the uterine cervix by inserting at least one pin into the uterine cervix According to some embodiments of the invention, the device further passes a needle through uterine cervix tissue.

According to some embodiments of the invention, the device includes a plurality of anchoring components, and further including suturing at least one of the anchoring components to the uterine cervix.

According to some embodiments of the invention, further including attaching the device to a cervix using adhesive silicone.

According to some embodiments of the invention, further including attaching the device to a cervix using biological glue.

According to an aspect of some embodiments of the present invention there is provided an insertion tool for inserting a device for retarding birth through a vagina.

According to an aspect of some embodiments of the present invention there is provided an insertion tool for inserting a device for retarding birth through a speculum in the vagina.

In some embodiments the insertion tool includes connector and/or connector rods for connecting to a device for retarding birth according to embodiments described herein.

In some embodiments the insertion tool is configured to deliver other devices through a lumen such as a vagina.

In some embodiments, the other devices are optionally approximately rings-shaped, or at least have an approximately ring-shaped base suitable for attaching to the insertion device.

In some embodiments the insertion tool is configured to contract its width across at least one cross-sectional dimension, potentially enabling to pass through a narrow lumen.

In some embodiments the insertion tool is optionally widened after having passed through the narrow lumen, optionally expanding and pushing sideways on the sides of the lumen after having passed through as a tool with a narrower form.

According to an aspect of some embodiments of the present invention there is provided an elongate tool for grasping a cervix through a vagina.

In some embodiments the grasping tool includes jaws for grasping suitable for reaching through a narrow lumen and opening at a distal end.

In some embodiments the jaws can optionally open up to 5 centimeters wide, while the grasping tool does not grow in width along most of its length, for example along more than 80% or 90% of its length.

In some embodiments the jaws are configured to expand to a width greater than 4 times a width of the elongate tool.

In some embodiments a width of the elongate tool is less than 1 centimeter, for example 0.8 centimeter, along more than 80% or 90% of its length, and the jaws can open up to 5 centimeters.

In some embodiments the grasping tool controls expansion of the jaws by a linear movement of controls along the elongate grasping tool, unlike, for example, scissors, where the handles move sideways to control opening of the scissors. Such example embodiments are described with reference to FIGS. 14A-E.

According to an aspect of some embodiments of the present invention there is provided a device for retarding birth, forming a lumen for surrounding a uterine cervix, the device including an upper ring for surrounding the uterine cervix, and an anchor for anchoring the device on the cervix.

According to some embodiments of the invention, an inner diameter of the upper ring is greater than an inner diameter of the anchor so that when an axial force is applied on the upper ring towards the anchor, the force generates a rotational force for rotating the anchor towards the cervix.

According to some embodiments of the invention, an inner diameter of the upper ring is greater than an inner diameter of the anchor so that when an axial force is applied on the upper ring towards the anchor, the force generates a rotational force for rotating the anchor towards the cervix.

According to some embodiments of the invention, the anchor is configured to anchor the device on the cervix non-invasively. According to some embodiments of the invention, the anchor includes a needle.

According to some embodiments of the invention, the anchor includes a plurality of anchoring components.

According to some embodiments of the invention, the upper ring is structured to leave empty spaces or gaps around the inner side of the upper ring so the empty spaces or gaps do not press on the cervix.

According to some embodiments of the invention, the plurality of anchoring components leaves empty spaces or gaps around the lumen for surrounding the cervix.

According to some embodiments of the invention, each one of the plurality of anchoring components includes a leg, and wherein the leg is configured to anchor against the cervix. The term leg is used herein for an extension from an upper portion of the device for retarding birth toward a lower portion of the device, which is a direction of the opening of the vagina, or vaginal introitus, when the device is located in place, gripping a cervix.

According to some embodiments of the invention, the plurality of anchoring components includes 3-7 anchoring components.

According to some embodiments of the invention, the upper ring is more rigid than the leg.

According to some embodiments of the invention, the leg is more rigid than the upper ring.

According to some embodiments of the invention, the leg is flexible.

According to some embodiments of the invention, further including a band surrounding the anchoring mechanism.

According to some embodiments of the invention, the band includes an elastic band to produce radial pressure of the anchors onto the cervix.

According to some embodiments of the invention, the band includes a metal ring.

According to some embodiments of the invention, the upper ring is elastic.

According to some embodiments of the invention, the upper ring includes a spring.

According to some embodiments of the invention, the upper ring includes a metal ring.

According to some embodiments of the invention, the upper ring includes a vibrating mechanism. In some embodiments the vibrating mechanism includes magnetic coils which vibrate when current is passed through. In some embodiments the vibration mechanism includes a motor and an off-center weight, producing vibration when the motor rotates. In some embodiments the device includes a battery for powering the vibrating mechanism.

In some embodiments the vibration mechanism includes an eccentric rotating mass that acts as an unbalanced mass on a (optionally DC) motor or a linear resonant actuator that contains a small internal mass attached to a spring, which creates a force when driven. The vibration can be a periodic, steady-state, transient or random vibration. The vibration can be harmonic or a non-harmonic.

According to some embodiments of the invention, the anchoring component includes a foot having a protrusion toward a cervix side, the protrusion having a shape selected from a group consisting of a single rectangular protrusion toward a cervix side, a spherical protrusion toward the cervix side, two rectangular protrusions toward the cervix side, and a hemispherical protrusion with the round side of the hemisphere toward the cervix side.

According to some embodiments of the invention, the protrusion is rigid.

According to some embodiments of the invention, the protrusion is flexible.

According to some embodiments of the invention, the anchoring components are distributed equi-distantly around the lumen.

According to some embodiments of the invention, the anchoring components are distributed non-equi-distantly around the lumen.

According to some embodiments of the invention, further including a sensor for measuring data from a group consisting of contractions, dilatation of a cervix, and progress of labor.

According to some embodiments of the invention, further including a transmitter for transmitting the data.

According to an aspect of some embodiments of the present invention there is provided a method for retarding birth including providing a device for retarding birth which forms a lumen for surrounding a uterine cervix, inserting the device into a vagina such that the lumen surrounds the uterine cervix, locating the device such that the upper ring surrounds the cervix in a fornix at a level of the cervical internal os, and placing the device such that the device grips the uterine cervix.

According to some embodiments of the invention, placing the device such that the device grips the uterine cervix includes placing the device to press the cervix and assist in preventing the cervix from opening, dilating and causing funneling of the cervix.

According to some embodiments of the invention, locating the device such that the upper ring surrounds the cervix in a fornix at a level of the cervical internal os includes locating the device such that the upper ring surrounds the cervix in a fornix within 5-30 millimeters from the level of the cervical internal os.

According to some embodiments of the invention, the device includes an upper ring for surrounding the uterine cervix and an anchoring mechanism for anchoring the device on the cervix.

According to some embodiments of the invention, the inserting includes changing a shape of the device to pass through a vaginal opening or through a vagina.

According to some embodiments of the invention, the inserting includes changing a shape of the device to pass through a speculum.

According to some embodiments of the invention, the inserting includes twisting the device to pass through a vaginal introitus.

According to some embodiments of the invention, the inserting includes twisting the device to pass through a speculum.

According to some embodiments of the invention, the locating of the device such that the upper ring surrounds the cervix includes releasing compression of the device to assist the device to surround the cervix.

According to some embodiments of the invention, the locating of the device such that the upper ring surrounds the cervix includes expanding the device to assist the device to surround the cervix.

According to some embodiments of the invention, the device further includes a band surrounding the device, and further including removing the band from around the device.

According to some embodiments of the invention, the removing of the band from around the device includes cutting the band.

According to some embodiments of the invention, the device grips the uterine cervix by pressing on the uterine cervix.

According to an aspect of some embodiments of the present invention there is provided a device for retarding birth, forming a lumen for surrounding a uterine cervix, the device including an upper ring for surrounding the uterine cervix, an anchoring mechanism for anchoring the device on the cervix, and a pivot location configured so that when the upper ring is pushed outward from an axis of the lumen, the upper ring rotates around the pivot and releases the anchoring of the device on the cervix.

According to some embodiments of the invention, the anchoring mechanism includes a plurality of anchoring components, each one of the plurality of anchoring components includes a leg, and the leg is configured to anchor against the cervix.

According to some embodiments of the invention, the pivot mechanism includes a band surrounding the anchoring mechanism.

According to an aspect of some embodiments of the present invention there is provided a tool for inserting a device for retarding birth, the device including a device lumen for surrounding a uterine cervix, the tool including a plurality of rods held by rings, forming a longitudinal, optionally circular, tool lumen, each rod including a connector for attaching to the device for retarding birth at a distal end of the rod, and a mechanism at a proximal end of the rod, for detaching the device for retarding birth at the distal end of the rod.

According to some embodiments of the invention, the rings are flexible, enabling a cross section of the longitudinal tool lumen to expand and contract.

According to some embodiments of the invention, the tool is configured to attach rings of different sizes, based on the cross section of the longitudinal tool lumen ability to expand and contract.

According to some embodiments of the invention, and further including a lever for moving the rods closer to each other, thereby shrinking a cross section of the tool lumen.

According to some embodiments of the invention, moving the rods causes the rings to changes an angle of attachment of the rods to the rings.

According to some embodiments of the invention, the lever for moving the rods closer to each other and/or causing inclination of the rods relative to the rings, moves one or more rods longitudinally relative to one or more other rods, thereby forming an oval cross section of the tool lumen.

According to some embodiments of the invention, further including a grip attached to at least one of the rods.

According to some embodiments of the invention, the lever is attached to a hinge included in the grip.

According to some embodiments of the invention in the insertion tool there are channels along the rods that enable allocation of biological glue or adhesive material or silicone to the legs of the device for retarding birth before release of the device, to glue the device to the cervix.

According to an aspect of some embodiments of the present invention there is provided a tool for grasping a cervix, the tool including two jaws for grasping a cervix, a hinge connecting the two jaws, enabling the jaws to separate and to close upon each other, an elongate tool connected to the two jaws, and controls for opening and closing the two jaws, wherein the jaws are configured to expand to a width greater than 4 times a width of the elongate tool.

According to some embodiments of the invention, each one of the two jaws includes a shape configured for grasping the cervix.

According to some embodiments of the invention, further including a scale for indicating a distance between the two jaws.

According to some embodiments of the invention, further including a scale for indicating an angle between the two jaws.

According to an aspect of some embodiments of the present invention there is provided a method for retarding birth including providing an insertion tool and a device for retarding birth attached to a distal end of the insertion tool, inserting the distal end of the insertion tool into a vagina, maneuvering the insertion tool so that the device surrounds a cervix, detaching the device from the insertion tool, leaving the device gripping the cervix, and withdrawing the insertion tool from the vagina.

According to some embodiments of the invention, the insertion tool is an insertion tool as descried herein.

According to some embodiments of the invention, the device for retarding birth is a device for retarding birth as described herein.

According to some embodiments of the invention, further including shrinking a cross section of the insertion tool lumen prior to inserting the distal end of the insertion tool into the vagina.

According to some embodiments of the invention, the inserting includes shrinking a cross section of the insertion tool lumen to pass through a speculum.

According to some embodiments of the invention, further including expanding the cross section of the insertion tool lumen prior to maneuvering the insertion tool so that the device surrounds a cervix.

According to some embodiments of the invention, further including maneuvering the device to grip the cervix as high as possible on the cervix.

According to some embodiments of the invention, the providing of the insertion tool as descried herein, with the device as described herein attached to a distal end of the insertion tool further includes providing a grasping tool as described herein inserted through a lumen of the insertion tool.

According to some embodiments of the invention, further including grasping the cervix with the grasping tool following the inserting of the distal end of the insertion tool into the vagina.

According to some embodiments of the invention, further including grasping the cervix with the grasping tool before the inserting of the distal end of the insertion tool into the vagina.

According to some embodiments of the invention, further including pulling the cervix with the grasping tool prior to the detaching the device from the insertion tool.

According to some embodiments of the invention, further including pushing the insertion tool so as to push the device up along the cervix prior to the detaching of the device from the insertion tool.

According to an aspect of some embodiments of the present invention there is provided a device for retarding birth, forming a lumen for surrounding a uterine cervix, the device including an upper ring for surrounding the uterine cervix, and an anchor for anchoring the device on the cervix.

According to some embodiments of the invention, an inner diameter of the upper ring is greater than an inner diameter of the anchor so that when an axial force is applied on the upper ring towards the anchor, the force generates a force that pushes the anchor towards the cervix.

According to some embodiments of the invention, the anchor is configured to anchor the device on the cervix non-invasively.

According to some embodiments of the invention, the anchor includes a needle.

According to some embodiments of the invention, the anchor includes a plurality of anchoring components.

According to some embodiments of the invention, the upper ring includes gaps around the inner side of the upper ring so the gaps do not press on the cervix.

According to some embodiments of the invention, the plurality of anchoring components leaves gaps around the lumen for surrounding the cervix.

According to some embodiments of the invention, the upper ring is elastic.

According to some embodiments of the invention, the upper ring includes a spring.

According to some embodiments of the invention, each one of the plurality of anchoring components includes a leg, and wherein the leg is configured to anchor against the cervix.

According to some embodiments of the invention, the plurality of anchoring components includes 3-7 anchoring components.

According to some embodiments of the invention, the leg is more rigid than the upper ring.

According to some embodiments of the invention, the leg is flexible.

According to some embodiments of the invention, further including a band surrounding the anchoring mechanism.

According to some embodiments of the invention, the band includes an elastic band to produce radial pressure of the anchors onto the cervix.

According to some embodiments of the invention, the band includes a spring.

According to some embodiments of the invention, the upper ring is elastic.

According to some embodiments of the invention, the upper ring includes a spring.

According to some embodiments of the invention, the upper ring includes a vibrating mechanism.

According to some embodiments of the invention, the upper ring includes a metal ring.

According to some embodiments of the invention, the anchoring component includes a foot having a protrusion toward a cervix side, the protrusion having a shape selected from a group consisting of a single rectangular protrusion toward a cervix side,
a spherical protrusion toward the cervix side, two rectangular protrusions toward the cervix side, and a hemispherical protrusion with the round side of the hemisphere toward the cervix side.

According to some embodiments of the invention, the protrusion is rigid.

According to some embodiments of the invention, the protrusion is flexible.

According to some embodiments of the invention, the anchoring components are distributed equi-distantly around the lumen.

According to some embodiments of the invention, the anchoring components are distributed non-equi-distantly around the lumen.

According to some embodiments of the invention, further including adhesive material on an inside of the anchoring component.

According to some embodiments of the invention, further including a sensor for measuring data from a group consisting of contractions, dilatation of a cervix, and progress of labor.

According to some embodiments of the invention, further including a transmitter for transmitting the data.

According to some embodiments of the invention, further including a component for eluting a drug.

According to an aspect of some embodiments of the present invention there is provided a method for retarding birth including providing a device for retarding birth which forms a lumen for surrounding a uterine cervix, inserting the device into a vagina such that the lumen surrounds the uterine cervix, locating the device such that the upper ring surrounds the cervix in a fornix at a level of the cervical internal os, and placing the device such that the device grips the uterine cervix.

According to some embodiments of the invention, placing the device such that the device grips the uterine cervix includes placing the device to press the cervix and assist in preventing the cervix from opening, dilating and causing funneling of the cervix.

According to some embodiments of the invention, locating the device such that the upper ring surrounds the cervix in a fornix at a level of the cervical internal os includes locating the device such that the upper ring surrounds the cervix in a fornix within 5 millimeters from the level of the cervical internal os.

According to some embodiments of the invention, the device includes an upper ring for surrounding the uterine cervix and an anchoring mechanism for anchoring the device on the cervix.

According to some embodiments of the invention, the inserting includes changing a shape of the device to pass through a vaginal opening.

According to some embodiments of the invention, the inserting includes changing a shape of the device to pass through a speculum.

According to some embodiments of the invention, the inserting includes twisting the device to pass through a vaginal opening.

According to some embodiments of the invention, the inserting includes twisting the device to pass through a speculum.

According to some embodiments of the invention, the locating the device such that the upper ring surrounds the cervix includes releasing compression of the device to assist the device to surround the cervix.

According to some embodiments of the invention, the locating the device such that the upper ring surrounds the cervix includes expanding the device for retarding birth to assist the device to more easily move up along the cervix.

According to some embodiments of the invention, the device further includes a band surrounding the device, and further including removing the band from around the device.

According to some embodiments of the invention, the device includes an upper ring for surrounding the uterine cervix and an anchoring mechanism for anchoring the device on the cervix.

According to some embodiments of the invention, the inserting includes changing a shape of the device to pass through a vaginal opening.

According to some embodiments of the invention, the inserting includes changing a shape of the device to pass through a speculum.

According to some embodiments of the invention, the inserting includes twisting the device to pass through a vaginal opening.

According to some embodiments of the invention, the inserting includes rotating the device to pass through a vaginal opening.

According to some embodiments of the invention, the inserting includes twisting the device to pass through a speculum.

According to some embodiments of the invention, the locating the device such that the upper ring surrounds the cervix includes releasing compression of the device to assist the device to surround the cervix.

According to some embodiments of the invention, the locating the device such that the upper ring surrounds the cervix includes expanding the device for retarding birth to assist the device to more easily move up along the cervix.

According to some embodiments of the invention, the device further includes a band surrounding the device, and further including removing the band from around the device.

According to some embodiments of the invention, removing the band from around the device includes cutting the band.

According to some embodiments of the invention, the device grips the uterine cervix by pressing on the uterine cervix.

According to an aspect of some embodiments of the present invention there is provided a device for retarding birth, forming a lumen for surrounding a uterine cervix, the device including an upper ring for surrounding the uterine cervix, an anchoring mechanism for anchoring the device on the cervix, and a pivot location configured so that when the upper ring is pushed outward from an axis of the lumen, the upper ring rotates around the pivot and releases the anchoring of the device on the cervix.

According to some embodiments of the invention, the anchoring mechanism includes a plurality of anchoring components, each one of the plurality of anchoring components includes a leg, and the leg is configured to anchor against the cervix.

According to some embodiments of the invention, the pivot mechanism includes a band surrounding the anchoring mechanism.

According to an aspect of some embodiments of the present invention there is provided an insertion tool for inserting a device for retarding birth, the device including a device lumen for surrounding a uterine cervix, the tool including a plurality of rods attached to at least two rings, forming a longitudinal tool lumen, each rod including a connector for attaching to the device for retarding birth at a distal end of the rod, and a mechanism at a proximal end of the rod, for detaching the device for retarding birth at the distal end of the rod.

According to some embodiments of the invention, the rods are flexibly attached to the rings, enabling a cross section of the longitudinal tool lumen to expand and contract.

According to some embodiments of the invention, the rings are flexible, enabling a cross section of the longitudinal tool lumen to expand and contract.

According to some embodiments of the invention, configured to attach devices for retarding birth of different sizes, based on the cross section of the longitudinal tool lumen ability to expand and contract.

According to some embodiments of the invention, further including a lever for moving the rods closer to each other, thereby shrinking a cross section of the tool lumen.

According to some embodiments of the invention, moving the rods causes the rings to changes an angle of attachment of the rods to the rings.

According to some embodiments of the invention, the lever for moving the rods closer to each other, moves one or more rods longitudinally relative to one or more other rods, thereby forming an oval cross section of the tool lumen.

According to some embodiments of the invention, the rods are configured to move apart from each other thereby expanding a cross section of the tool lumen and expanding an attached device for retarding birth.

According to some embodiments of the invention, the rods includes channels along the rods for dispensing adhesive material to a device for retarding birth.

According to some embodiments of the invention, further including a grip attached to at least one of the rods.

According to some embodiments of the invention, the lever is attached to a hinge included in the grip.

According to an aspect of some embodiments of the present invention there is provided a grasping tool for grasping a cervix, the tool including two jaws for grasping a cervix, a hinge connecting the two jaws, enabling the jaws to separate and to close upon each other, an elongate tool connected to the two jaws, and controls for opening and closing the two jaws, wherein the jaws are configured to expand to a width greater than 4 times a width of the elongate tool.

According to some embodiments of the invention, the controls are configured to move linearly along a direction of an axis of the elongate tool when opening and closing the jaws.

According to some embodiments of the invention, each one of the two jaws includes a shape configured for grasping the cervix.

According to some embodiments of the invention, further including a scale for indicating a distance between the two jaws.

According to some embodiments of the invention, further including a scale for indicating an angle between the two jaws.

According to an aspect of some embodiments of the present invention there is provided a method for retarding birth including providing an insertion tool and a device for retarding birth attached to a distal end of the insertion tool, inserting the distal end of the insertion tool into a vagina, maneuvering the insertion tool so that the device surrounds a cervix, detaching the device from the insertion tool, leaving the device gripping the cervix, and withdrawing the insertion tool from the vagina.

According to some embodiments of the invention, the insertion tool is an insertion tool as described herein.

According to some embodiments of the invention, the device for retarding birth is a device for retarding birth as described herein.

According to some embodiments of the invention, further including shrinking a cross section of a lumen of the insertion tool prior to inserting the distal end of the insertion tool into the vagina.

According to some embodiments of the invention, the inserting includes shrinking a cross section of the lumen of the insertion tool to pass through a speculum.

According to some embodiments of the invention, further including expanding the cross section of the lumen of the insertion tool prior to maneuvering the insertion tool so that the device surrounds a cervix.

According to some embodiments of the invention, further including maneuvering the device to grip the cervix as high as possible on the cervix.

According to some embodiments of the invention, the providing the insertion tool as described herein, with the device as described herein attached to a distal end of the insertion tool further includes providing a grasping tool as described herein inserted through a lumen of the insertion tool.

According to some embodiments of the invention, further including grasping the cervix with the grasping tool following the inserting of the distal end of the insertion tool into the vagina.

According to some embodiments of the invention, further including grasping the cervix with the grasping tool before the inserting of the distal end of the insertion tool into the vagina.

According to some embodiments of the invention, further including pulling the cervix with the grasping tool prior to the detaching of the device from the insertion tool.

According to some embodiments of the invention, further including pushing the insertion tool so as to push the device up along the cervix prior to the detaching of the device from the insertion tool.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 13A and 13B are simplified illustrations of a device for retarding birth according to an example embodiment of the invention;

FIGS. 13C and 13D are simplified illustrations of a device for retarding birth according to an example embodiment of the invention;

FIGS. 13E-I are simplified illustrations of a device for retarding birth according to an example embodiment of the invention;

FIGS. 14A and 14B are simplified illustrations of a cervix grasping tool according to an example embodiment of the invention;

FIGS. 17A-C, which are simplified illustrations of a device for retarding birth placed around a uterine cervix according to an example embodiment of the invention;

DESCRIPTION OF SPECIFIC EMBODIMENTS OF THE INVENTION

Figures 1A, 1B:
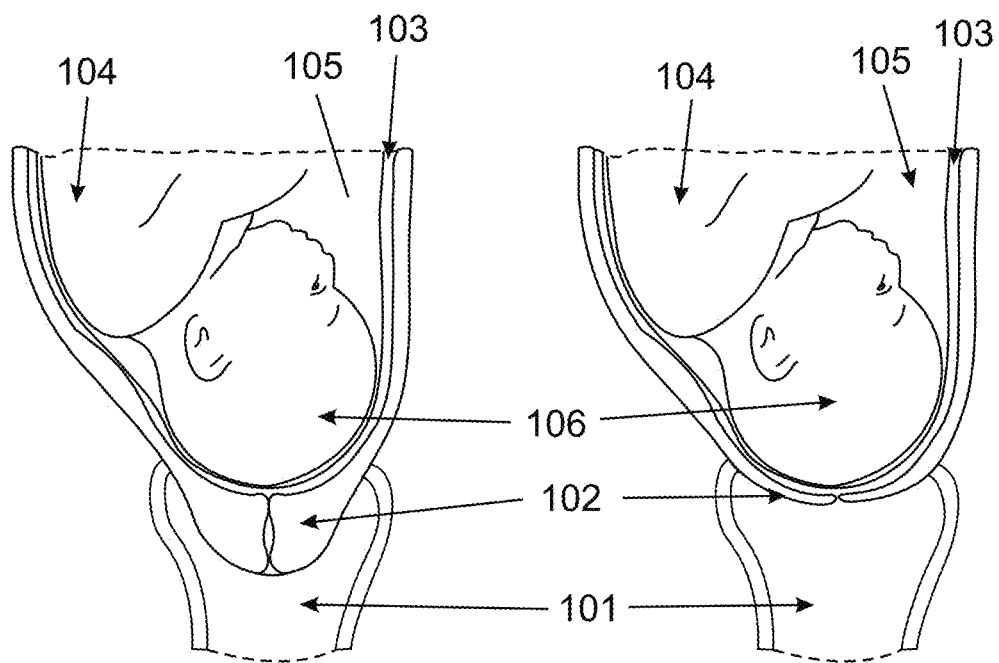
FIGS. 1A-1B are simplified illustrations of a process of birth.

The present invention, in some embodiments thereof, relates to devices and methods for delaying pre-term birth or pre-term delivery and, more particularly, but not exclusively, to devices inserted into the vagina and surrounding the cervix and to related methods.

In some embodiments the devices optionally include pessaries.

Overview

An aspect of some embodiments of the invention relates to a device for encircling a cervix, with an anchoring mechanism which increases pressure on the cervix corresponding to force applied on an upper ring which encircles the cervix.

In some embodiments, a rotational force is produced on multiple anchoring components, around a pivot point or line or around a pivot component.

In some embodiments, during contraction the upper ring of the device is pushed. This creates a force that is re-directed around the pivot point/line as a rotational force on the anchoring components.

In some embodiments, during contraction the upper ring of the device is pushed. This creates a force that is directed to the anchoring component, optionally causing the anchoring component to bend inward, closing a lumen and gripping the cervix.

In some embodiments the pivot is a tip of the anchoring component(s) which presses against external tissue of the cervix. When the pressure of the anchoring component(s) increases, a friction force between the anchoring component(s) and the cervix tissue increases, and a counterforce that keeps the upper ring in its place increases.

In some embodiments the anchoring mechanism optionally pierces cervix tissue with a needle and sutures the device to the cervix.

In some embodiments the anchoring mechanism optionally pierces cervix tissue with pins.

In some embodiments the device is optionally attached to a cervix using an adhesive such as silicone or other polymer adhesive or gel or biological glue.

In some embodiments the adhesive serves to anchor the device.

In some embodiments the adhesive assists in anchoring the device.

In some embodiments the device is optionally glued to a cervix using biological glue.

In some embodiments the biological glue serves to anchor the device.

In some embodiments the biological glue assists in anchoring the device.

In some embodiments the pivoting is around legs designed to surround the cervix, and feet of the legs designed to anchor against the cervix. Pressing outward and/or downward on the upper ring potentially causes the legs to pivot inward and press upon the cervix.

In some embodiments the pivoting is around a band surrounding multiple legs, the legs designed to surround the cervix, and feet of the legs designed to anchor against the cervix. Pressing outward and/or downward on the upper ring potentially causes the legs to pivot inward and press upon the cervix.

In some embodiments the number of legs is three, four, five, six or more.

In some embodiments there are equal gaps between all the legs.

In some embodiments some of the gaps between the legs are of different sizes. By way of a non-limiting example, in some embodiments there are six legs, and the gaps at "3 o'clock" and at "9 o'clock" are larger than the other gaps.

In some embodiments there are gaps between the legs, leaving some areas of a surface of the cervix without pressing components, potentially easing blood flow in the cervix, potentially easing venous blood flow, which is near a surface of the cervix.

In some embodiments the upper ring is constructed to hold onto the cervix at several sections of a circumference of the cervix, leaving other sections of the circumference of the cervix without pressing components, potentially easing blood flow in the cervix, potentially easing venous blood flow, which is near a surface of the cervix.

In some embodiments the device is marked to indicate one or more specific sides of the device, intended to indicate to a physician inserting the device in what direction the device should be inserted and/or in what direction the device should be positioned to grip the cervix.

In some embodiments the device is marked at "12 o'clock" and/or at "6 o'clock". The marking positions are described relative to how the physician should observe the marking(s) when the device is positioned correctly on the cervix.

In some embodiments the device is marked with echogenic, radiopaque or other contrast material to allow detecting the place of the device on the cervix using ultrasound, x-ray, CT, MRI or other medical imaging method.

In various embodiments, various different devices may be provided, such as, by way of some non-limiting examples:
- with different radii of the upper ring, optionally ranging from a sharp edge to a radius of 3 mm, 5 mm, 7 mm, 10 mm;
- with different thickness of the upper ring optionally ranging from 3 to 15 mm;
- with different shapes of the outer part of the upper ring which may be circular or not circular but of other shapes such as rectangular, oblong, triangular, oval or with protrusions that may be evenly or unevenly spaced around the upper ring;
- with different elasticities of the upper ring, optionally ranging from 20 to 90 shore A;
- with different firmness of the material of the upper ring. In some embodiments the upper ring may comprise of an inner ring with a higher hardness, by way of a non-limiting example 70 shore A, and an outer layer of a softer elastomer, by way of a non-limiting example 20 shore A. In some embodiments the upper ring may also comprise an inner metal spring covered by a softer material;
- with different radii of a lumen defined by the anchoring component;
- with different radii of a lumen defined between anchoring legs;
- with different lengths of anchoring legs, for example 5-40 mm below the upper ring;

with different width of the anchoring legs;

with different durability of the legs, by way of a non-limiting example 20 shore A up to completely rigid;

with different elasticity of the legs; and with different elasticity of an elastic band for compressing the legs onto a cervix.

In some embodiments the legs may be rigid and rotatably attached to the upper ring.

In some embodiments the elastic band has a Shore A hardness in a range of 20-90.

In some embodiments the component called the elastic band comprises a metal spring or a metal band.

In some embodiments the elastic band is attached to the legs of the device.

In some embodiments the elastic band is comprises within a sleeve surrounding the legs of the device.

An aspect of some embodiments of the invention relates to a device for grasping a cervix, with an upper component for grasping the cervix on a top side and an anchoring component lower down along the cervix.

An aspect of some embodiments of the invention relates to a device for grasping a cervix, with an anchoring mechanism, in which an upper component which grasps the cervix is designed to expand under pressure, and optionally pivot around a pivot line or ring or component, thereby releasing the cervix. Such pivoting may occur in various embodiments shown in the Figures, and is shown in more detail in FIG. 18A and its description.

In some embodiments the device includes the upper component and legs for anchoring onto the cervix lower along the cervix.

In some embodiments the device includes the upper component, legs for anchoring onto the cervix lower along the cervix, and a band for compressing the legs onto the cervix.

In some embodiments, the upper component expands under sideways or downward pressure, the legs anchor onto the cervix, the upper ring flips over, pivots or turns, inverting the device and the legs upon the cervix, thereby weakening or releasing the anchoring, enabling the device to slip off the cervix under the above-mentioned pressure.

In some embodiments the upper component is in a shape of a ring.

In some embodiments the upper component includes an inner lumen for grasping and pressing onto certain sections of the cervix, and leaving other sections free, without pressure, potentially easing blood flow through at least the free sections.

In some embodiments the upper component includes projections for pressing onto the cervix.

In some embodiments the upper component is shaped as an oval, a triangle, a rectangle, a pentagon, a hexagon, some other shape with N straight sides, as a three-pointed star or as an N-pointed star.

An aspect of some embodiments of the invention relates to a device for encircling a cervix, with an upper ring designed to encircle a cervix, legs designed to point lower down along the cervix, and a band for compressing the legs onto the cervix.

In some embodiments the band presses the legs onto the cervix, thereby anchoring the device onto the cervix.

In some embodiments the device may not have a band around the legs, and the device anchors onto the cervix without the band.

In some embodiments the upper ring serves to press the cervix and assist in preventing the cervix from opening, dilating and causing funneling of the cervix at a level of the internal os of the cervix or below that level.

In some embodiments the band serves to press the legs upon the cervix and assist in preventing the cervix from opening.

In some embodiments both the upper ring serves to press the cervix and assist in preventing the cervix from opening and the band serves to press the legs upon the cervix and assist in preventing the cervix from opening.

In some embodiments the band is optionally elastic.

In some embodiments the device is placed around the cervix, pressing onto and closing the cervix. When a time comes to release the device, e.g. when the physicians finds it necessary either when reaching term or before term due to other medical indications, a physician optionally cuts the band, releasing some or all of the pressure of the legs upon the cervix.

In some embodiments when a time comes to release the device, e.g. when the physicians finds it necessary either when reaching term or before term due to other medical indications, a physician optionally cuts the ring, releasing some or all of the pressure of the device upon the cervix and enabling removal.

An aspect of some embodiments of the invention relates to using a tool for inserting via the vagina, to grasp a cervix.

In some embodiments the cervix grasping tool is optionally inserted through a speculum in the vagina to hold and grasp a cervix.

In some embodiments the cervix grasping tool is optionally used to grasp a cervix and pull the cervix in order to allow insertion of a device for delaying preterm birth and positioning the device for delaying preterm birth at a higher position on the cervix.

In some embodiments the cervix grasping tool optionally includes a scale upon which a physician can measure a distance or angle or similar measurement which measured an extent to which the grasping tool is open when grasping the cervix. In some embodiments the measurement is optionally used to measure a diameter and/or size of the cervix.

In some embodiments, the scale provides data to be used when selecting a device for delaying pre-term birth or pre-term delivery. The data may be provided as an angle to which the grasping tool is opened; as a distance to which jaws of the grasping tool are opened; as a number which represents a size of device or a size of upper ring of the device for delaying pre-term birth; or as an arbitrary number.

In some embodiments the data is used to select a size of device or a size of upper ring of the device for delaying pre-term birth.

In some embodiments one or two jaws of the grasping tool optionally include wheels which can be used to pull the cervix into the jaws.

An aspect of some embodiments of the invention relates to an insertion tool for inserting a device for delaying pre-term birth or pre-term delivery.

In some embodiments the device is attached to the insertion tool, and the insertion tool is used to insert the device via a vagina and onto a cervix.

In some embodiments the device is attached to the insertion tool, and the insertion tool is used to insert the device via a speculum in the vagina and onto the cervix.

In some embodiments the insertion tool compresses the device, in order to present a smaller cross section when inserting via the vagina.

In some embodiments the insertion tool is configured to stop compressing the device, enabling the device to expand next to the cervix.

In some embodiments the insertion tool includes two or more parallel rods, which are configured to be manipulated to slide longitudinally relative to each other. In some embodiments the insertion tool includes two, three, four, five, six, seven, eight or more parallel rods.

In some embodiments the insertion tool is configured so that when the parallel rods are manipulated to slide longitudinally relative to each other, a distance between the rods is changed, collapsing or expanding.

In some embodiments the insertion tool is configured so that when the parallel rods are manipulated to slide longitudinally relative to each other, the rods converge more at one end of the lumen than another.

In some embodiments the rods are connected to each other by rings. In some embodiments the rings are flexible. In some embodiments the rings are rigid.

In some embodiments the rods are connected to each other by straps or links. In some embodiments the straps or links are flexible. In some embodiments the straps or links are rigid.

In some embodiments, a flexibility of the rings/straps/links around the rods allows there to be variability in the distance or circumference of the distal parts of the rods and thus potentially enables attaching different rings of different sizes, all on a same device.

In some embodiments the insertion tool is configured to enable pushing the device onto the cervix.

In some embodiments the insertion tool is configured to detach from the device when the device has been placed onto the cervix.

In some embodiments the insertion tool is attached to the device at more than one location.

In some embodiments the insertion tool is configured to be detached from the device from more than one location, one location or more at a time.

In some embodiments the insertion tool is configured to be detached from the device from all the attaching locations at once.

In some embodiments the insertion tool compresses the device, in order to present a smaller cross section when inserting via a speculum in the vagina.

According to some embodiments of the invention the insertion tool includes channels along the rods that allow allocation of biological glue or adhesive material or silicone to the legs of the device for retarding birth before its release to allow gluing to the cervix.

An aspect of some embodiments of the invention relates to using both a grasping tool and an insertion tool, for grasping a cervix and sliding a device for delaying pre-term birth or pre-term delivery over the cervix.

In some embodiments the grasping tool is used to pull the cervix towards an operator holding the grasping tool.

In some embodiments the grasping tool is used to pull the cervix toward the device.

In some embodiments the cervix is held in place, and the insertion tool is used to push the device over the cervix.

In some embodiments the cervix is pulled toward an operator and the insertion tool is used to push the device over the cervix. In some embodiments the cervix is pulled toward the operator and the insertion tool is simultaneously used to push the device over the cervix.

In some embodiments the cervix is pulled toward the device and the insertion tool is simultaneously used to push the device, either simultaneously or in consecutive movements, optionally to position the device well situated in the fornix, around and over the cervix.

The terms "up", "top" and "upper" in all their grammatical forms are used throughout the present specification and claims to describe a direction towards the uterus.

The terms "down", bottom and "lower" in all their grammatical forms are used throughout the present specification and claims to describe a direction away from the uterus, toward the vagina and the exit of the vagina.

When the above directions are applied to a device which is outside of the body, the directions "up" and "down" apply to directions of the device as if it is inserted into a body.

In some embodiments the device is inserted into a vagina so that the upper ring surrounds the cervix, optionally at a level of the vaginal fornix, in proximity to the cervical internal os.

In some embodiments the device is inserted into a vagina so that the upper ring surrounds the cervix and is pushed up high into the fornix.

In some embodiments a method of inserting the device optionally includes surrounding the cervix by the upper ring, then pushing up on the anchoring mechanism.

In some embodiments, by limiting cervical dilatation, the biological cascade which leads to a common pathway of parturition characterized by cervical remodeling, cervical ripening, uterine contractility and fetal membrane activation is slowed or even prevented.

In some embodiments when the uterus contracts, pushing the amniotic sac in which the fetus is situated, in direction of the cervix and causing funneling, the ring redirects a force produced, to exert a closing force upon the internal os of the cervix and potentially decreases funneling.

In some embodiments, by applying the closing force on the cervix in response to contractions, the biological cascade that leads to a common pathway of parturition characterized by cervical remodeling, cervical ripening, uterine contractility and fetal membrane activation is slowed or even prevented.

In some embodiments the ring is designed to provide a progressive; a linear; a degressive; or a constant force for closing the internal os of the cervix when the uterus contracts.

An aspect of some embodiments of the invention includes providing an anchoring mechanism for the device, where the anchoring mechanism is arranged to increase the anchoring extension's hold on a surface of the patient's body.

In some embodiments the anchoring mechanism may include protrusions for increasing friction between the anchoring mechanism and a surface of a cervix against which the device is placed.

In some embodiments the anchoring mechanism may include an adhesive component such as silicone or other polymer adhesive or gel for increasing friction between the anchoring mechanism and a surface of a cervix against which the device is placed.

In some embodiments the anchoring mechanism may include biological glue.

In some embodiments the anchoring mechanism may be anchored or partially anchored by friction against the vaginal walls.

An aspect of some embodiments of the invention relates to anchoring a device to a lower portion of a cervix, while a top of the device narrows the cervical opening.

In some embodiments the device includes a lumen which surrounds the uterine cervix.

In some embodiments a length of the lumen of the device is approximately equal to a length of the uterine cervix. In some embodiments a length of the lumen of the device is smaller than a length of the uterine cervix.

In some embodiments an upper ring in the device is designed to be smooth, so that when the baby's head applies force, the force is spread around and does not apply concentrated force to any particular place on the cervix-potentially preventing tears.

Some potential benefits of using an anchoring mechanism include:

In some embodiments, no suture is required, and the device is easily and simply deployed, potentially without anesthesia, and potentially in an out-patient or clinic procedure.

In some embodiments, suturing is optionally used, but less suturing may be required, potentially resulting in a simpler procedure, potentially without need for general anesthesia, potentially resulting in less damage to the sutured organ, and potentially resulting in better device retention.

In some embodiments, automatic suturing is optionally used, potentially resulting in a simpler procedure, potentially without the need for general anesthesia potentially resulting in less damage to the sutured organ, and potentially resulting in better device retention.

In some embodiments the device is a disposable device placed in the vagina around the uterine cervix.

In some embodiments the device is positioned by a physician in an outpatient clinic.

In some embodiments the device is positioned by a physician in the hospital.

In some embodiments the device is positioned by a physician in a procedure lasting a few minutes.

In some embodiments the device is removed at term by a physician.

In some embodiments the device is removed before term, or at term, or whenever a physician deems necessary.

In some embodiments the device is removed by a physician in a procedure lasting a few minutes.

In some embodiments the device optionally measures and gathers data regarding contractions, dilatation of the cervix and progress of labor.

In some embodiments the device optionally transfers the data by wireless communication, e.g. Bluetooth technology or other wireless technology, to an external receiver.

In some embodiments the device optionally includes a contraction sensing component, such as, by way of a non-limiting example, a strain gauge. In some embodiments the device optionally includes a signal amplifier for amplifying signals from the contraction sensing component.

In some embodiments the device optionally transmits a contraction signal via RF to an external receiver.

In some embodiments the RF communication device includes a Bluetooth transmitter, and optionally transmits a contraction signal to an external Bluetooth receiver (not shown). In some embodiments the external Bluetooth receiver (not shown) may be included in a device such as smartphone for real time contraction monitoring by the doctor and/or the patient.

In some embodiments the device optionally includes memory for storing measurements.

In some embodiments the device optionally includes a contraction sensing component, such as, by way of a non-limiting example, a strain gauge. In some embodiments the device optionally includes a signal amplifier for amplifying signals from the contraction sensing component.

In some embodiments the device is optionally drug eluting, optionally drugs for delaying or progressing labor.

In some embodiments the device optionally gathers data regarding preterm birth.

In some embodiments the device optionally gathers data regarding the condition of the fetus.

In some embodiments, one or more of the above benefits may potentially be implemented.

Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways.

Reference is now made to FIGS. 1A-1B, which are simplified illustrations of a process of birth.

A main function of a cervix 102 is its role in childbirth. As a fetus 104 descends in preparation for birth, a presenting part, usually the head 106, rests on and is supported by the cervix 102. The fetus 104 is in the amniotic sac surrounded by amniotic fluid 105. This stage is depicted by FIG. 1A.

This support begins to give way as the cervix 102 starts to dilate. This stage is depicted by FIG. 1B.

During childbirth, the cervix 102 must dilate to a diameter greater than the fetal head 106 or fetal buttock—the exact size depends on the gestational age as it is pushed from the uterus 103 to the vagina 101.

Toward childbirth the cervix 102 also becomes shorter, known as effacement.

Figure 2:
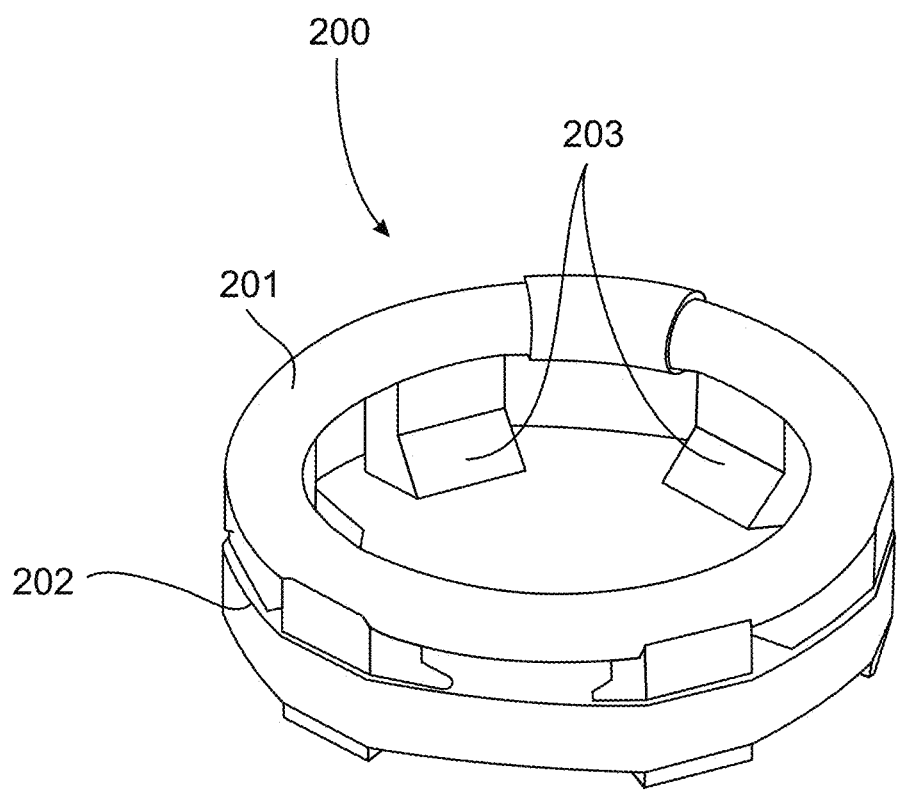
FIG. 2 is a simplified illustration of a device for retarding birth according to an example embodiment of the invention.

Reference is now made to FIG. 2, which is a simplified illustration of a device for retarding birth according to an example embodiment of the invention.

FIG. 2 shows a device 200 which includes an upper ring 201 for surrounding a uterine cervix; an anchoring mechanism 203 for anchoring the device on the cervix.

In some embodiments, the upper ring 201 is constructed of silicone. In some embodiments, the upper ring 201 includes a silicone tube.

FIG. 2 also shows a band 202 surrounding the device 200. In some embodiments the band 202 is elastic. In some embodiments the band 202 is rigid.

In some embodiments the anchoring mechanism 203 converts force on the upper ring to inward radial force on the anchoring mechanism 203.

In some embodiments a downward force on the upper ring 201 is redirected as rotational force inward on the anchoring mechanism 203, with an internal tip of the anchoring mechanism, which is in contact with an outer surface of a uterine cervix, acting as a hinge at one or more points or along a line.

In some embodiments the device 200 is a single-use device, placed in a vagina around the uterine cervix, and disposed of after one use.

In some embodiments the device 200 is flexible, configured to be compressed longitudinally, that is, in a top-bottom direction.

In some embodiments the device 200 is flexible, configured to be elongated longitudinally, that is, in a top-bottom direction.

In some embodiments the device 200 can be elongated longitudinally, that is, in a top-bottom direction.

In some embodiments the device 200 is flexible, configured to be compressed sideways, that is, in a direction of decreasing diameter.

In some embodiments the device 200 is flexible, configured to be expanded sideways, that is, in a direction of increasing diameter.

Figure 3:
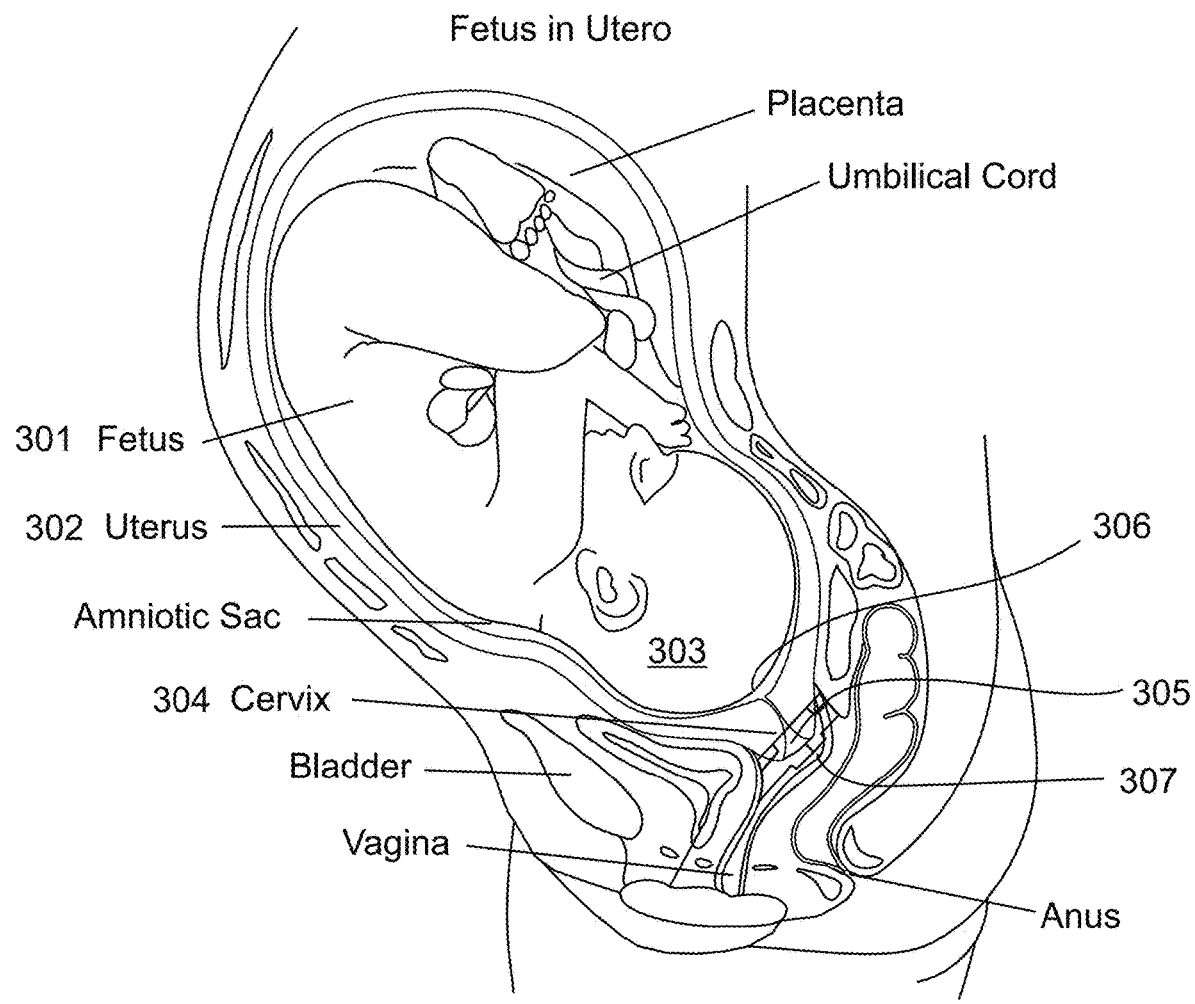
FIG. 3 is a simplified cross-sectional illustration of a pregnancy with a device for retarding birth located around a uterine cervix according to an example embodiment of the invention.

Reference is now made to FIG. 3, which is a simplified cross-sectional illustration of a pregnancy with a device for retarding birth located around a uterine a cervix according to an example embodiment of the invention.

FIG. 3 shows a fetus 301 in a uterus 302. The fetus 301 head 303 is located on an upper os 306 of the uterine cervix 304, called the internal os. A device 305 for retarding birth surrounds the uterine cervix, optionally above a lower os 307, called the external os, of the uterine cervix 304.

In some embodiments the device 305 acts as an elastic securing mechanism, helping to hold the uterine cervix closed before birth is due, to help prevent or to delay pre-term birth.

In some embodiments the device 305 is configured to allow transient shortening of the cervix during contractions.

Figure 4A:
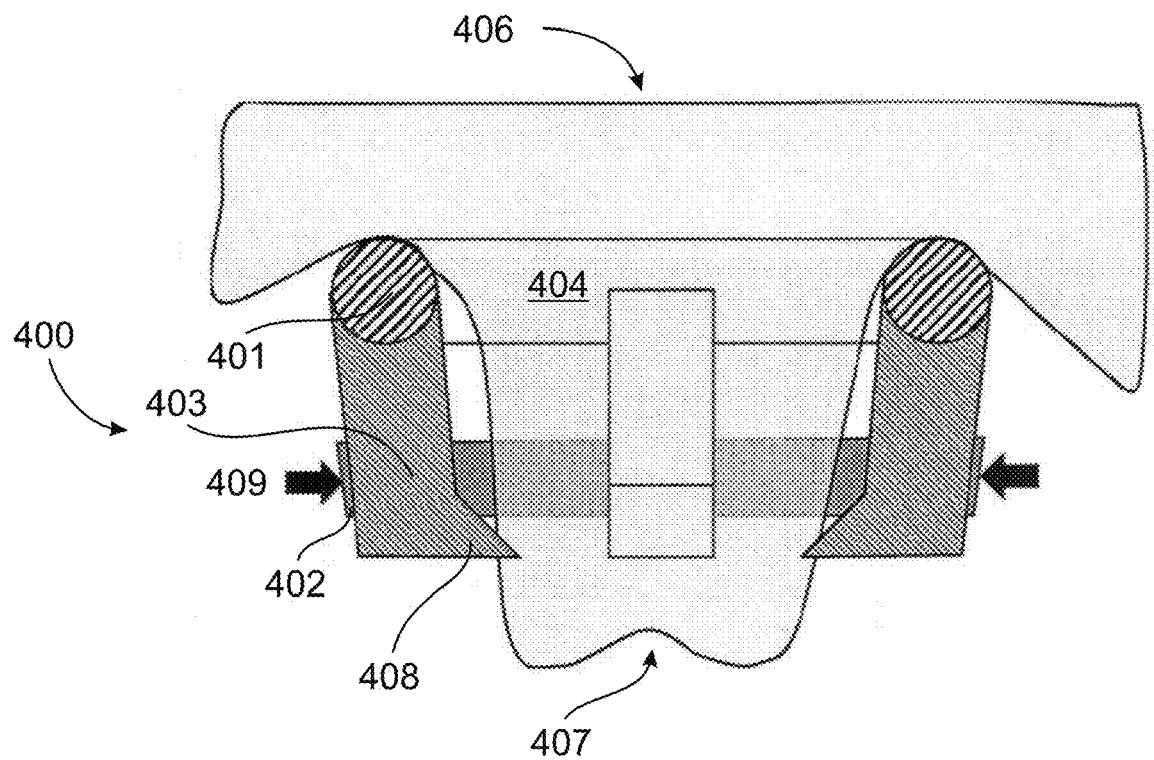
FIGS. 4A and 4B are simplified cross-sectional illustrations of a device for retarding birth placed around a uterine cervix according to an example embodiment of the invention.
Figure 4B:
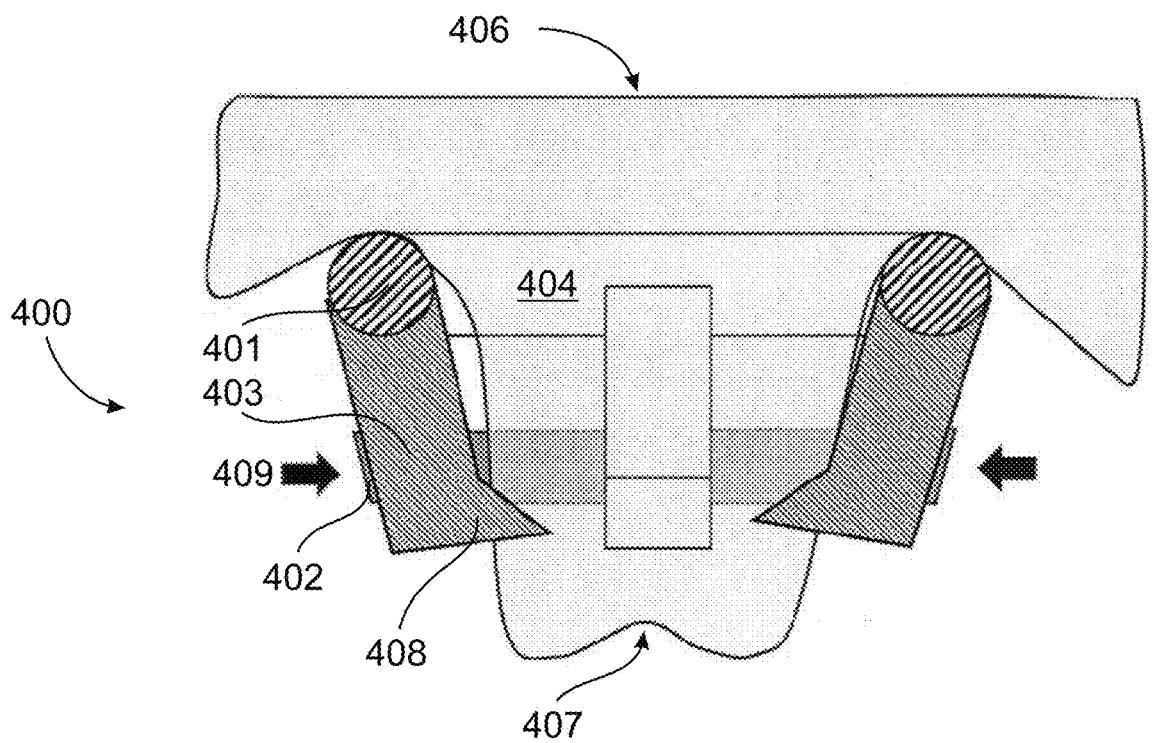

Reference is now made to FIGS. 4A and 4B, which are simplified cross-sectional illustrations of a device for retarding birth placed around a uterine cervix according to an example embodiment of the invention, FIGS. 4A and 4B show the device 400 with an upper ring 401 for surrounding a uterine cervix 404; and an anchoring mechanism 403 for anchoring the device 400 on the cervix 404.

In some embodiments the anchoring mechanism 403 redirects or converts force on the upper ring 401 to inward radial force 409 on the anchoring mechanism 403.

In some embodiments the anchoring mechanism 403 includes several arms.

FIGS. 4A and 4B also shows an optional band 402 surrounding the device 400, optionally keeping components of the anchoring mechanism 403 of the device 400 from expanding radially outward.

FIGS. 4A and 4B also show an approximate location of an internal os 406 of the uterine cervix 404 and an external os 407 of the cervix 404.

In some embodiments when the fetus head or amniotic sac presses down on the upper ring 401, an anchoring effect of the anchoring mechanism 403 on the cervix 404 prevents the device 400 from slipping down along the cervix 404.

In some embodiments a tip or tips 408 of the anchoring mechanism 403 optionally acts as a hinge, causing the anchoring mechanism 403 to push radially inward, exerting force on the cervix 404, in response to a downward force on the upper ring 401.

In some embodiments the band 402 optionally acts as a hinge, causing the anchoring component 403 to push radially inward, exerting force on the cervix 404, in response to a downward force on the upper ring 401.

In some embodiments the band 402 optionally acts as a hinge, causing the anchoring component 403 to push radially inward, exerting force on the cervix 404, in response to an outward force on the upper ring 401.

In some embodiments the upper ring 401 includes a spring which exerts force to dilate the upper ring 401, causing the anchoring component 403 to push radially inward, exerting force on the cervix 404, in response to the opening force on the upper ring 401.

Figure 5A:
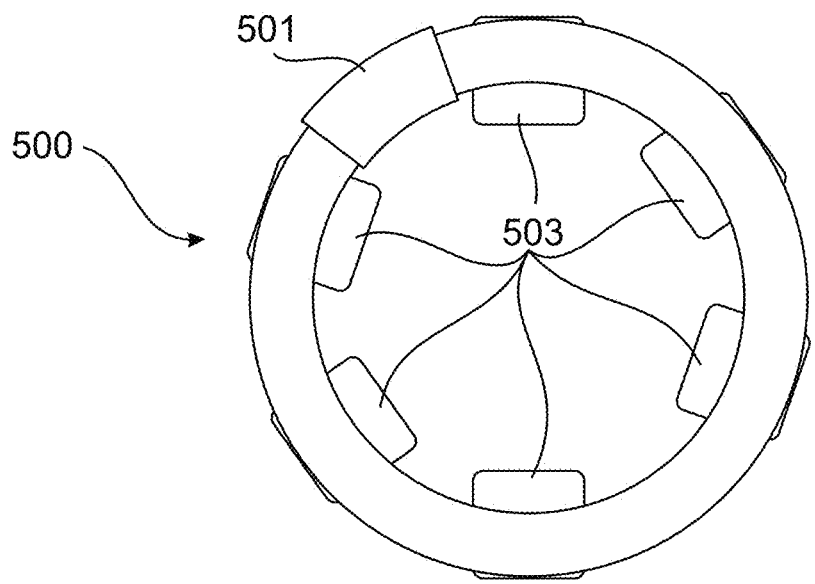
FIGS. 5A-5C are simplified illustrations of a device for retarding birth according to an example embodiment of the invention.
Figure 5B:
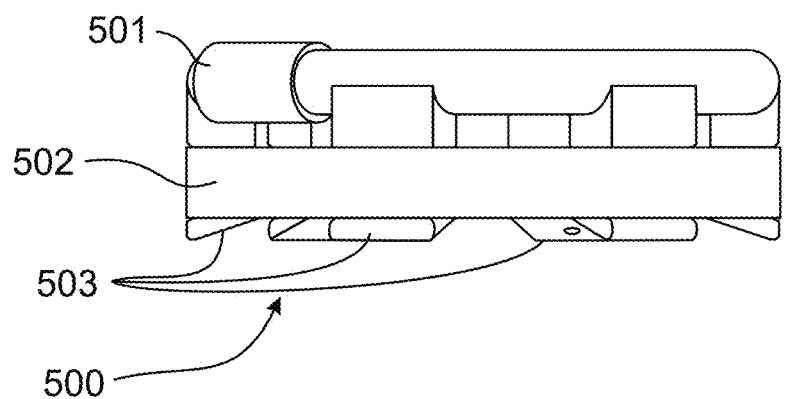
Figure 5C:
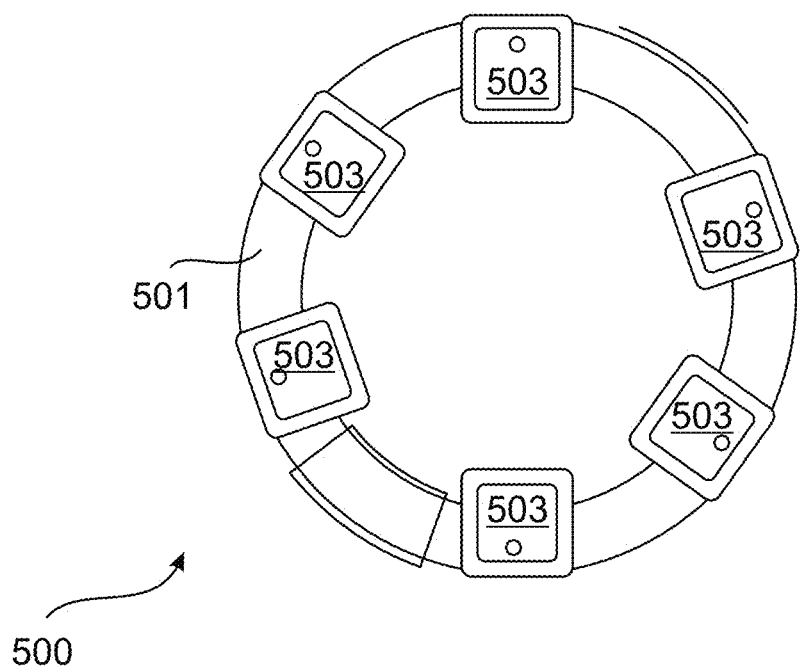

Reference is now made to FIGS. 5A-5C, which are simplified illustrations of a device for retarding birth according to an example embodiment of the invention.

FIG. 5A is a top view of a device 500 for retarding birth, FIG. 5B is a side view of the device 500, and FIG. 5C is a bottom view of the device 500.

With reference to FIGS. 5A-5C, the term top view means a view in a direction from a uterus toward a vagina, and the term bottom view mean in an opposite direction.

FIGS. 5A-5C show the device 500 including an upper ring 501; and anchoring components 503 for anchoring the device 500 on the cervix, FIGS. 5A-5C also show an optional band 502 for optionally keeping the anchoring components 503 of the device 500 from expanding radially outward.

The number of anchoring components 503 included in an anchoring mechanism of the device 500 can range from a small number, even one or two, to a large number, for example 20 and above.

In some embodiments the number of anchoring components is an even number, in a range from two to twenty inclusive.

In some embodiments the number of anchoring components is an uneven number in a range from three to twenty one inclusive.

In some embodiments the anchoring components are evenly spaced around a lumen defined by the upper ring.

In some embodiments the anchoring components are not evenly spaced around a lumen defined by the upper ring.

In some embodiments the band 502 is elastic.

In some embodiments the band 502 is rigid. In some embodiments the band 502 is semi-rigid.

In some embodiments the band 502 includes a spring.

The device 500 is optionally constructed in different sizes, diameters and heights.

A typical diameter of the device is optionally 32 millimeters (mm), ranging from small, for example 10 mm or 20 mm, to larger, for example 40 mm, 50 mm, 60 mm, and larger, according to a patient's size, intended patient (human or animal) and medical considerations.

Figure 6A:
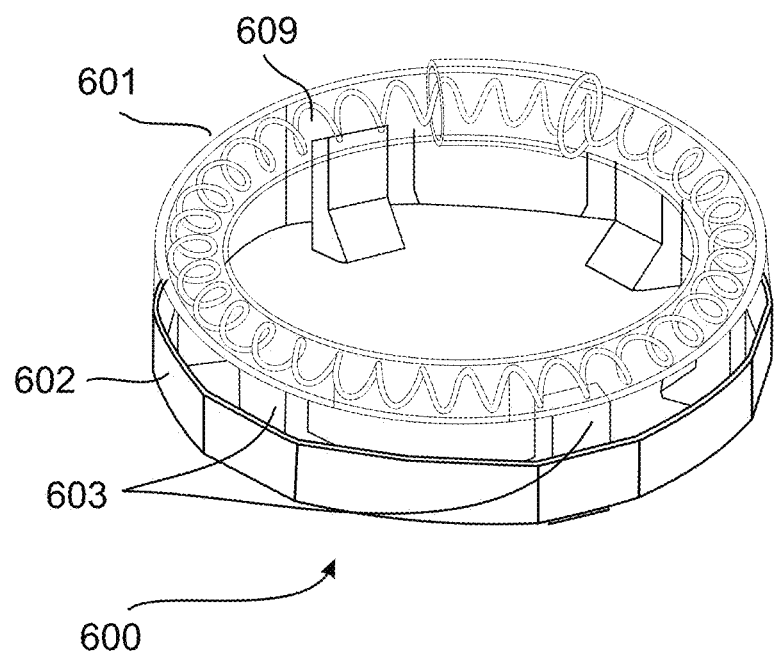
FIGS. 6A and 6B are simplified illustrations of a device for retarding birth according to an example embodiment of the invention.
Figure 6B:
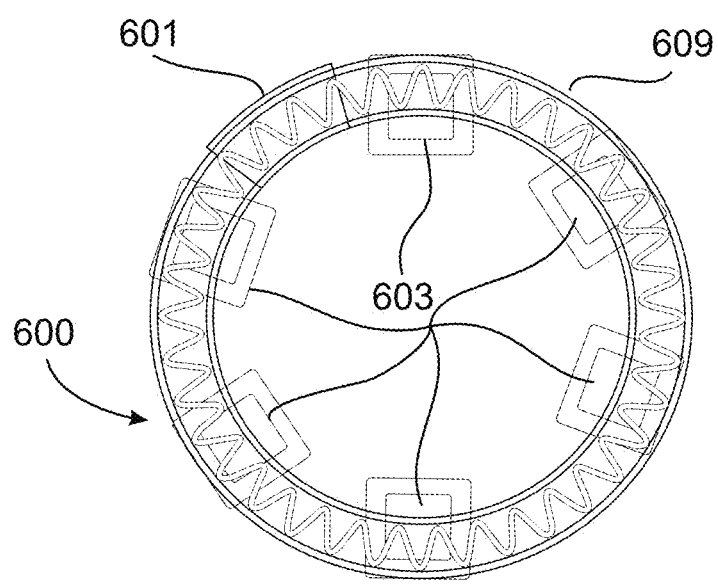

Reference is now made to FIGS. 6A and 6B, which are simplified illustrations of a device for retarding birth according to an example embodiment of the invention.

FIG. 6A is an isometric top view of a device 600 for retarding birth, and FIG. 6B is a top view of the device 600.

With reference to FIGS. 6A and 6B, the term top view means a view in a direction from a uterus toward the outlet of a vagina, and the term bottom view mean in an opposite direction.

FIGS. 6A and 6B show the device 600 including an upper ring 601 and anchoring components 603 for anchoring the device 600 on the cervix, FIGS. 6A and 6B also show an optional band 602 for optionally keeping components of the anchoring mechanism 603 of the device 600 from expanding radially outward.

In some embodiments the upper ring 601 includes a spring 609. In some embodiments the upper ring 601 includes a flexible tube surrounding the spring 609.

Figure 7A:
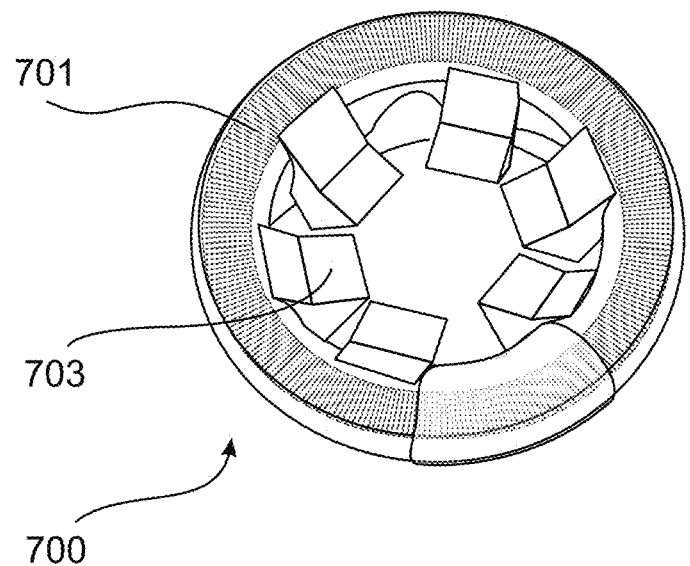
FIGS. 7A and 7B are images of example embodiments of devices for retarding birth according to an example embodiment of the invention.
Figure 7B:
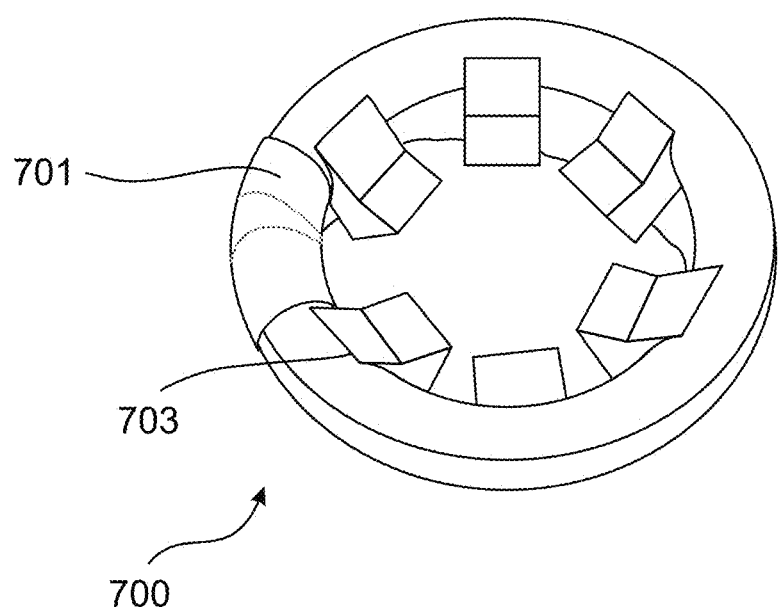

Reference is now made to FIGS. 7A and 7B, which are images of example embodiments of devices for retarding birth according to an example embodiment of the invention.

FIGS. 7A and 7B are top views of a device 700 for retarding birth.

With reference to FIGS. 7A and 7B, the term top view means a view in a direction from a uterus toward a vagina.

FIGS. 7A and 7B show the device 700 including an upper ring 701 and anchoring components 703 for anchoring the device 700 on the cervix.

FIGS. 7A and 7B are intended to show that spacing between the anchoring components 703 for anchoring the device 700 on the cervix may be different in different embodiments.

Figure 8B:
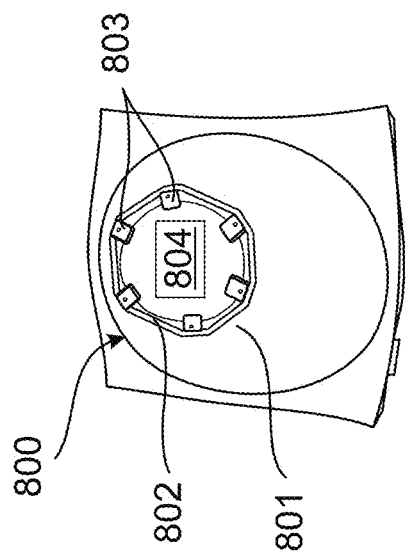
FIGS. 8A and 8B are images of a device for retarding birth placed around a model of a uterine cervix according to an example embodiment of the invention.
Figure 8A:
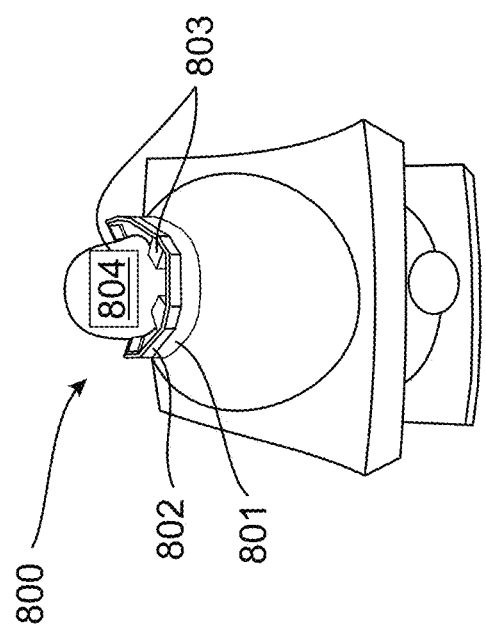

Reference is now made to FIGS. 8A and 8B, which are images of a device for retarding birth placed around a model of a uterine cervix according to an example embodiment of the invention.

FIGS. 8A and 8B show a device 800 encircling or embracing a lab model of a uterine cervix 804.

FIGS. 8A and 8B are isometric views of the device 800 and the lab model of the cervix 804.

FIGS. 8A and 8B are shown upside-down relative to the previous Figures, with the "top" point down and the "bottom" pointing up.

FIGS. 8A and 8B show the device 800 including an upper ring 801, anchoring components 803; and an optional band 802, for optionally keeping components of an anchoring mechanism of the device 800 from expanding radially outward.

Reference is now made to FIGS. 9A-9D, which are simplified illustrations of anchoring components for a device for retarding birth according to example embodiments of the invention.

FIGS. 9A-9D show different embodiments of different anchoring components 900 910 920 930.

The anchoring components 900 910 920 930 include a top side configured to match a shape of an upper ring (not shown in FIGS. 9A-9D but shown in prior drawings).

Each one of the anchoring components 900 910 920 930 shown in FIGS. 9A-9D shows a different anchoring component foot 903 913 923 933 designed for providing anchoring against a surface of a cervix (not shown).

Figure 9B:
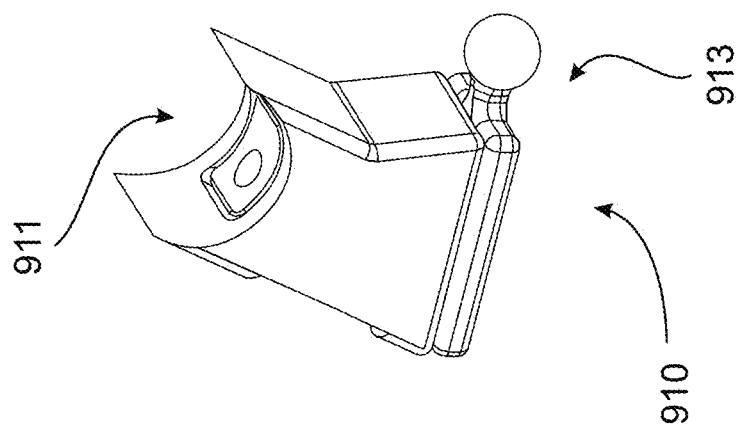
FIGS. 9A-9D are simplified illustrations of anchoring components for a device for retarding birth according to example embodiments of the invention.
Figure 9A:
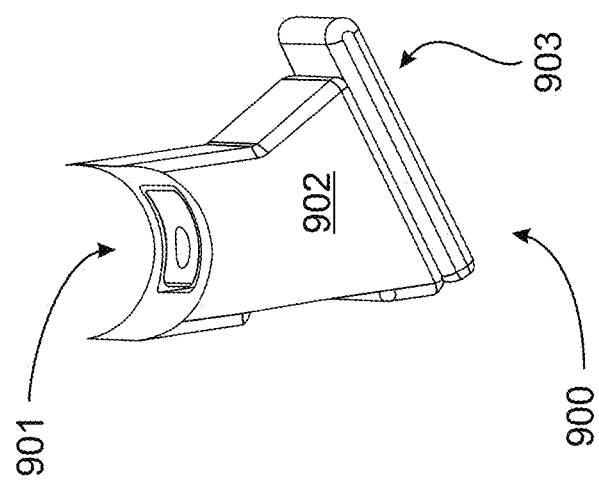

FIG. 9A shows the anchoring component foot 903 with a single rectangular protrusion toward a cervix side.

FIG. 9B shows the anchoring component foot 913 with a spherical protrusion toward a cervix side.

Figure 9D:
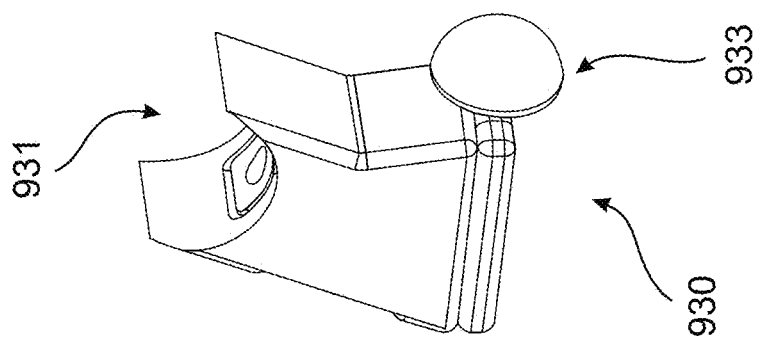
Figure 9C:
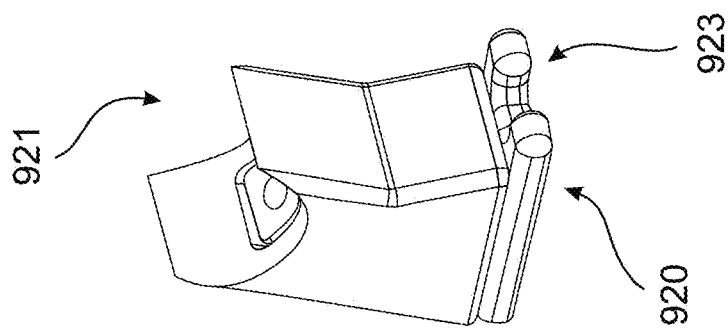

FIG. 9C shows the anchoring component foot 903 with two rectangular protrusions toward a cervix side.

FIG. 9D shows the anchoring component foot 903 with a single hemispherical protrusion, with the round side of the hemisphere toward a cervix side.

In some embodiment (not shown), the anchoring component includes one or more pins for penetrating some distance into the cervix. A length of the pin(s) is optionally in a range between 0.5 mm and 5 mm.

In some embodiments protrusions to the anchoring component are designed for anchoring on an inside lumen of the device, against an outside surface of the cervix.

In some embodiments a shape of the anchoring component which is designed to be against the inside lumen of the device, against the outside surface of the cervix, is optionally designed for gluing with biological glue and/or an adhesive such as silicone or other polymer adhesive or gel.

In some embodiments a shape of the anchoring component which is designed to be against the inside lumen of the device, against the outside surface of the cervix, is optionally designed for friction, by way of a non-limiting example by having multiple protrusions, by a rough surface, and so on.

In some embodiments a shape of the anchoring component which is designed to be against a surface of the vagina is optionally designed for friction, by way of a non-limiting example by having protrusions, by having multiple protrusions, by including pins, by being suitable for gluing, by using adhesive such as silicone or other polymer adhesive or gel, by a rough surface, and so on.

Reference is now made to FIGS. 10A-10E, which are simplified illustrations of a device for retarding birth according to an example embodiment of the invention.

Figure 10C:
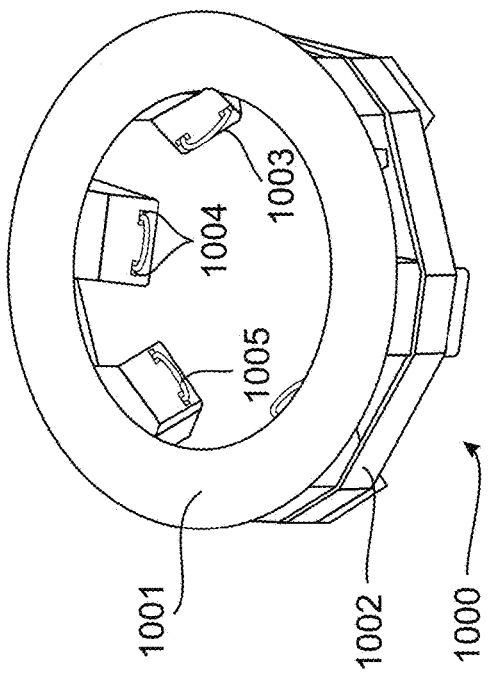
FIGS. 10A-10E are simplified illustrations of a device for retarding birth according to an example embodiment of the invention.
Figure 10D:
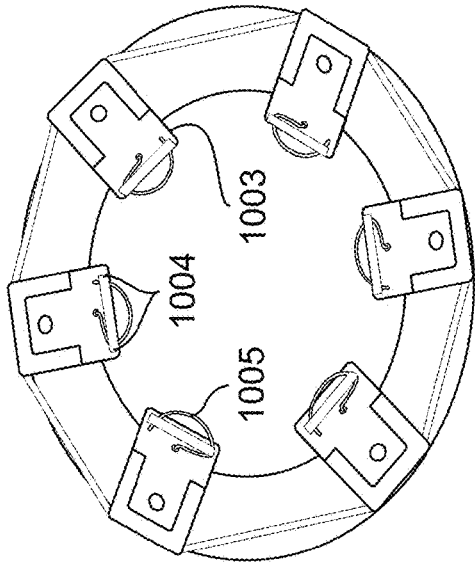
Figure 10A:
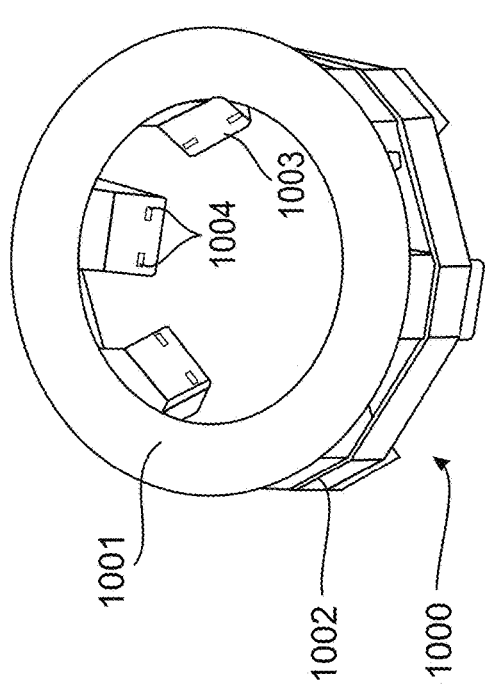

FIG. 10A shows a device 1000 including an upper ring 1001, anchoring components 1003.

FIG. 10A is an isometric top view, and with reference to FIG. 10A, the term top view means a view in a direction from a uterus toward a vagina.

FIG. 10A also shows an optional band 1002 surrounding the device 1000, optionally keeping components of the anchoring mechanism 1003 of the device 1000 from expanding radially outward.

FIG. 10A is intended to show an example embodiment of anchoring component(s) 1003 which includes slots 1004 for optionally enabling a needle and/or suture thread (not shown in FIG. 10A) to pass therethrough.

Figure 10B:
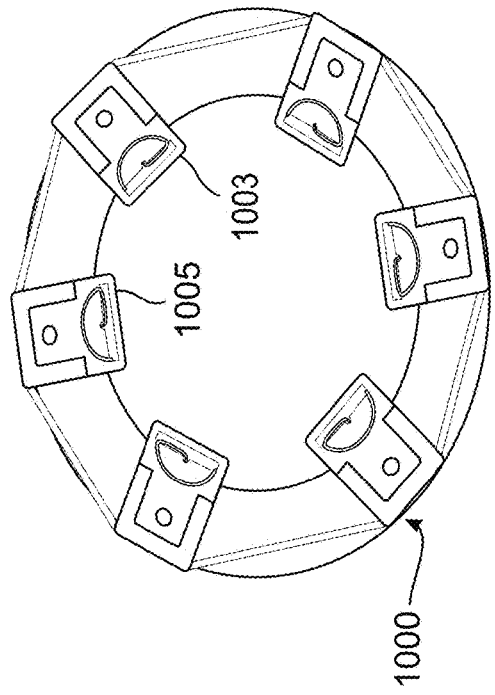

FIG. 10B is an isometric bottom view, in an opposite direction of FIG. 10A.

FIG. 10B shows the device 1000, with additional detail in the anchoring components 1003.

FIG. 10B shows a view of internal components of the anchoring components 1003, and a suturing needle 1005 stored therein.

In some embodiments the suturing needle 1005 is optionally extruded through one of the slots 1004 to penetrate cervix tissue, potentially assisting in anchoring the device 1000.

In some embodiments the suturing needle 1005 is optionally extruded through one of the slots 1004, penetrates cervix tissue, and a tip of the suturing needle 1005 returns back into another one of the slots 1004, potentially assisting in anchoring the device 1000 and/or covering the sharp tip of the suturing needle 1005.

In some embodiments extrusion of the suturing needle 1005 through a slot 1004 is optionally operated by a tool, optionally by a caregiver who operates the tool.

In some embodiments the suturing needle 1005 is optionally packaged in the anchoring component 1003 with a mechanism which, when operated and/or released and/or triggered, activates the suturing needle 1005 to pass through cervix tissue.

FIG. 10C shows the device 1000 including the upper ring 1001 and the anchoring components 1003.

FIG. 10C is an isometric top view, similar to FIG. 10A.

FIG. 10C also shows the optional band 1002.

FIG. 10C is intended to show the example embodiment of anchoring component(s) 1003 and shows the suturing needle 1005 passed through a first slot 1004 and a tip of the suturing needle 1005 passed back through a second slot 1004.

FIG. 10D shows the device 1000, with additional detail in the anchoring components 1003.

FIG. 10D is an isometric bottom view, in an opposite direction of FIG. 10C.

FIG. 10D shows a view of internal components of the anchoring components 1003, and the suturing needle 1005.

FIG. 10D shows an example embodiment where a tip of the suturing needle 1005 passed through the first slot 1004 and passed back through the second slot 1004.

Figure 10E:
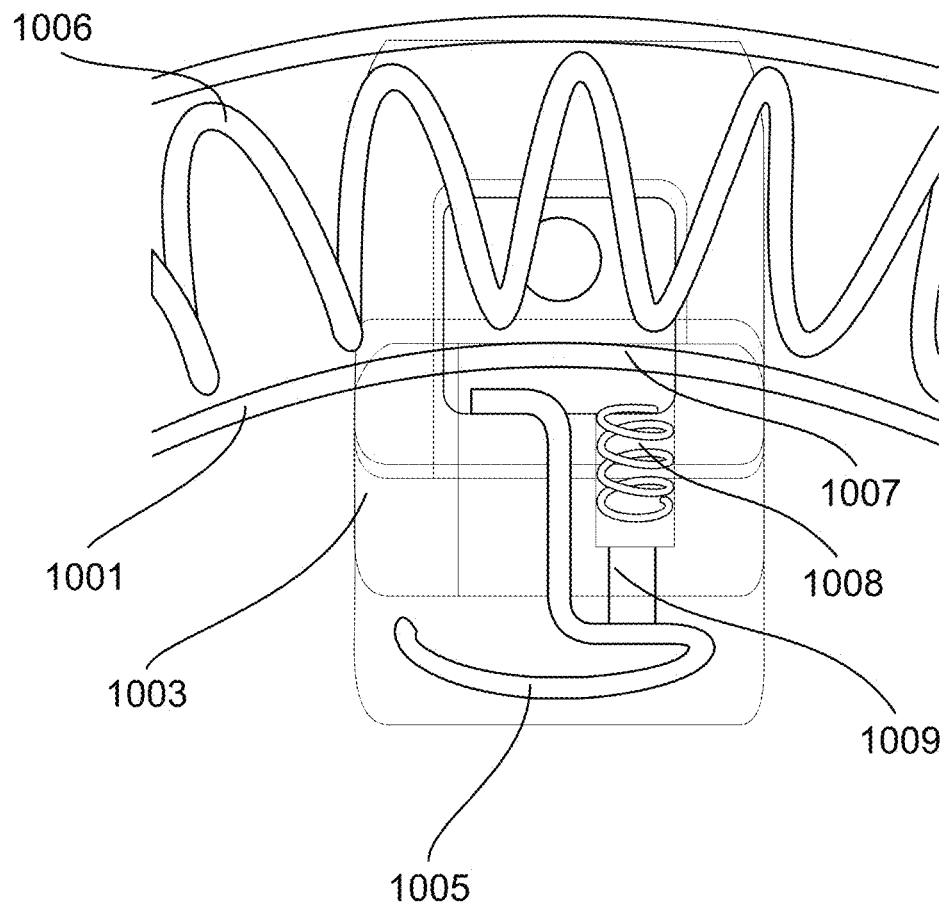

FIG. 10E shows a view of internal components of the anchoring component 1003, and the suturing needle 1005 stored therein.

In some embodiments the suturing needle 1005 is optionally activated by a mechanism 1007 which rotates the suturing needle 1005 to suture cervix tissue.

In some embodiments the suturing needle 1005 is optionally activated by releasing a stop 1009 which optionally blocks movement of the suturing needle 1005 until activation. In some embodiments the stop 1009 is activated to release the suturing needle 1005 by pressing against a spring 1008.

FIG. 10E shows and example embodiment with a spring 1006 included in the upper ring 1001.

Figure 11A:
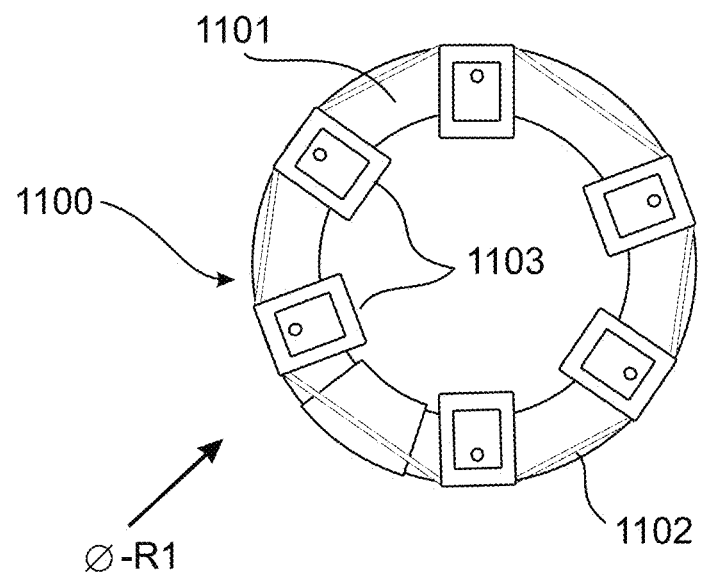
FIGS. 11A-11C are simplified illustrations of a device for retarding birth according to an example embodiment of the invention.
Figure 11B:
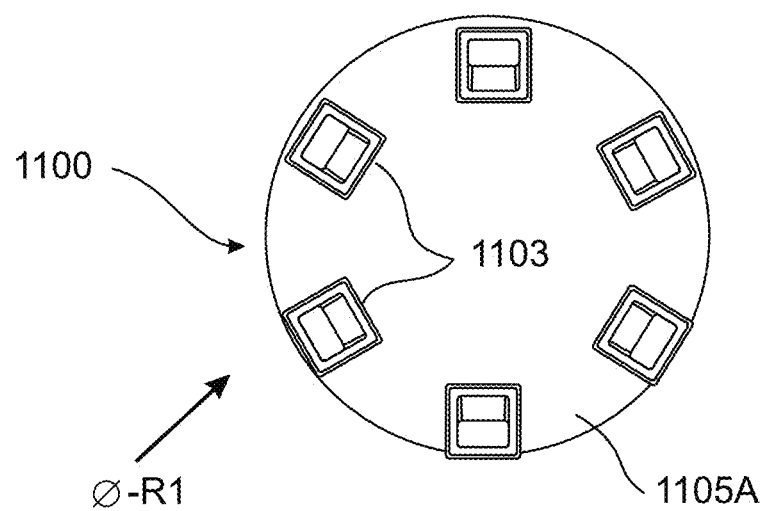
Figure 11C:
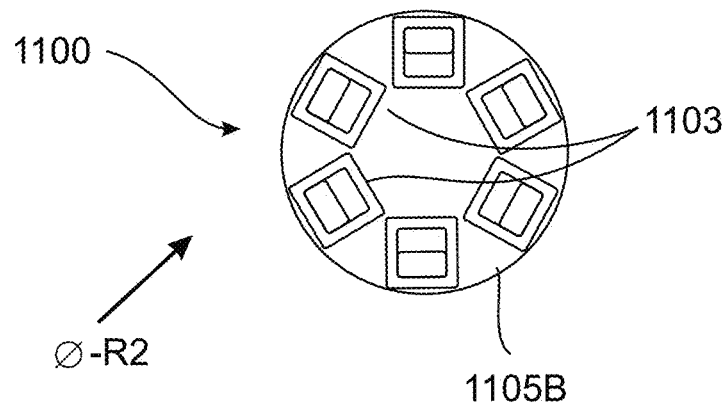

Reference is now made to FIGS. 11A-11C, which are simplified illustrations of a device for retarding birth according to an example embodiment of the invention.

FIGS. 11A-11C are bottom views of a device 1100 for retarding birth.

With reference to FIGS. 11A-11C, the term bottom view means a view in a direction from a vagina toward a uterus.

FIGS. 11A-11C show the device 1100 including an upper ring 1101; anchoring components 1103; and an optional band 1102.

FIG. 11A shows the device 1100 having a first diameter R1.

FIG. 11B shows the device 1100 having the same first diameter R1. FIG. 11B is a more simplified view, which shows the anchoring components 1103 and a circle 1105 (which exists in the drawing, not necessarily in the device 1100) which emphasizes the first diameter R1.

FIG. 11C shows the device 1100 after compression to a second diameter R2. FIG. 11C shows the anchoring components 1103 and a smaller circle 1105B (which exists in the drawing, not necessarily in the device 1100) which emphasizes the second diameter R2. FIG. 11C shows an exemplary second diameter R2 smaller than the first diameter R1.

It is noted that the device 1100 can optionally be expanded to have a diameter (not shown) greater than the first diameter R1.

Figure 12:
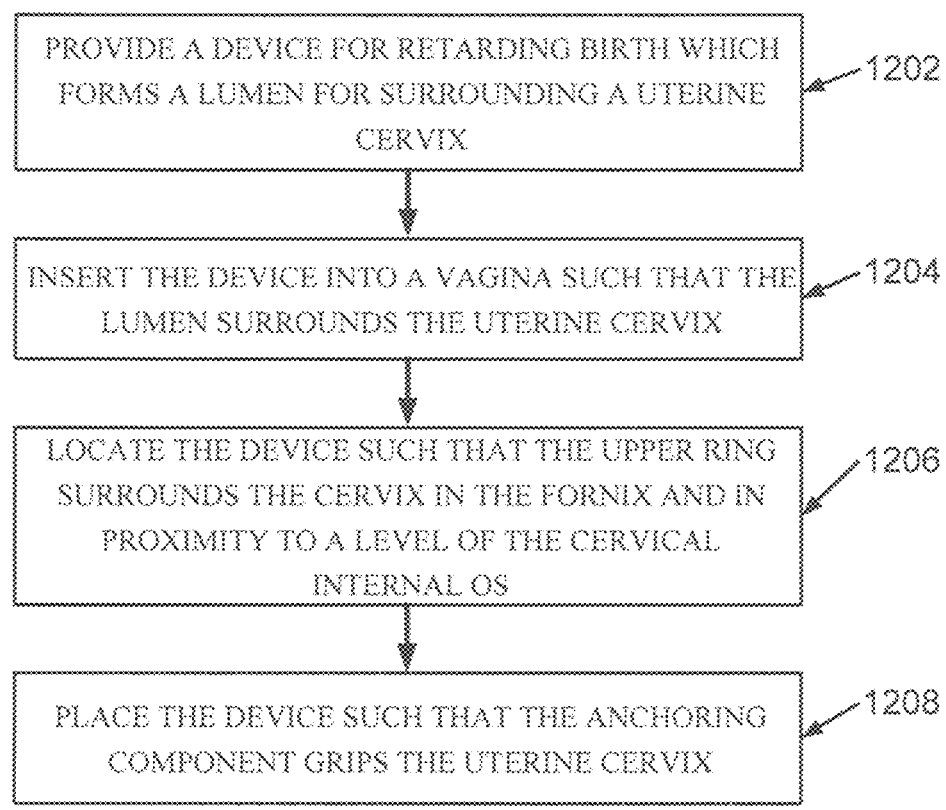
FIG. 12 is a simplified flowchart illustration of a method for retarding birth according to another example embodiment of the invention.

Reference is now made to FIG. 12, which is a simplified flowchart illustration of a method for retarding birth according to another example embodiment of the invention.

The method of FIG. 12 includes:
providing a device for retarding birth which forms a lumen for surrounding a uterine cervix (1202);
inserting the device into a vagina such that the lumen surrounds the uterine cervix (1204);
locating the device such that the upper ring surrounds the cervix in the fornix and in proximity to the level of the cervical internal os (1206); and
placing the device such that the anchoring component grips the uterine cervix (1208).

In some embodiments the device includes:
an upper ring for surrounding the uterine cervix; and
an anchoring mechanism for anchoring the device on the cervix.

In some embodiments the device includes an optional band, optionally keeping components of the anchoring mechanism from expanding radially outward.

In some embodiments the method includes compressing the device to pass through a vaginal opening.

In some embodiments the method includes releasing compression of the device to assist the device to surround the cervix.

In some embodiments the locating the device includes urging or pushing the device up so that the upper ring surrounds the cervix in the fornix and in proximity to the level of the cervical internal os.

In some embodiments the method includes expanding the device to assist the device to surround the cervix.

In some embodiments the method includes releasing the expanding of the device.

In some embodiments the method includes the anchoring mechanism gripping the uterine cervix by pressing on the uterine cervix.

In some embodiments the anchoring method includes an adhesive such as: silicone, some other polymer adhesive, gel.

In some embodiments the method includes the anchoring mechanism anchoring to the uterine cervix by inserting at least one pin into the uterine cervix.

In some embodiments the method includes the anchoring mechanism passing a needle through uterine cervix tissue.

In some embodiments the method includes suturing at least one of the anchoring components to the uterine cervix.

Reference is now made to FIGS. 13A and 13B, which are simplified illustrations of a device for retarding birth according to an example embodiment of the invention.

FIGS. 13A and 13B show a device for retarding birth which includes an upper ring 1301 for encircling a cervix, connectors 1304 for connecting the upper ring to anchoring pads 1303, a spring 1305, a band 1306 and protrusions 1302.

In some embodiments the spring 1305 is used for pushing apart the upper ring 1301 and the anchoring pads 1303 and/or the band 1306.

In some embodiments the spring 1305 is kept compressed when the device is inserted into a vagina and positioned to encircle a cervix, and optionally released when the anchoring pads 1303 grip the cervix, optionally as high as possible along the cervix.

In some embodiments, following release of the spring 1305, the upper ring 1301 is pushed toward a top of the cervix against the anchoring of the anchoring pads 1303.

Reference is now made to FIGS. 13C and 13D, which are simplified illustrations of a device for retarding birth according to an example embodiment of the invention.

FIGS. 13C and 13D show a device for retarding birth which includes an upper ring 1311 for encircling a cervix, anchoring rings 1313 1314, anchoring prongs 1317, and a spring 1316.

In some embodiments the spring 1316 is used for pushing apart the upper ring 1311 and the anchoring rings 1313 1314.

In some embodiments the spring 1316 is kept compressed when the device is inserted into a vagina and positioned to encircle a cervix, and optionally released when the anchoring rings 1313 1314 grip the cervix, optionally as high as possible along the cervix.

In some embodiments, following release of the spring 1316, the upper ring 1311 is pushed toward a top of the cervix against the anchoring of the anchoring rings 1313 1314.

Reference is now made to FIGS. 13E-I, which are simplified illustrations of a device for retarding birth according to an example embodiment of the invention.

FIGS. 13E-I show a device which includes an upper ring 1321 for surrounding a uterine cervix; and an anchoring mechanism for anchoring the device on the cervix. The anchoring mechanism includes legs 1323, feet 1325 for pressing against a cervix and gripping the cervix, and a band 1324 for pressing the feet against the cervix.

Figure 13E:
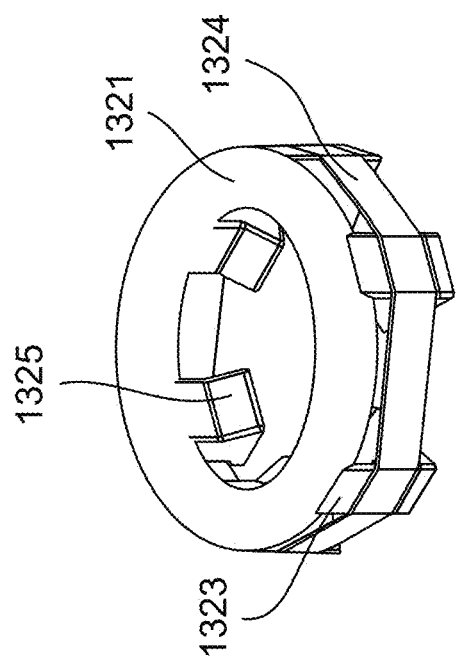
Figure 13F:
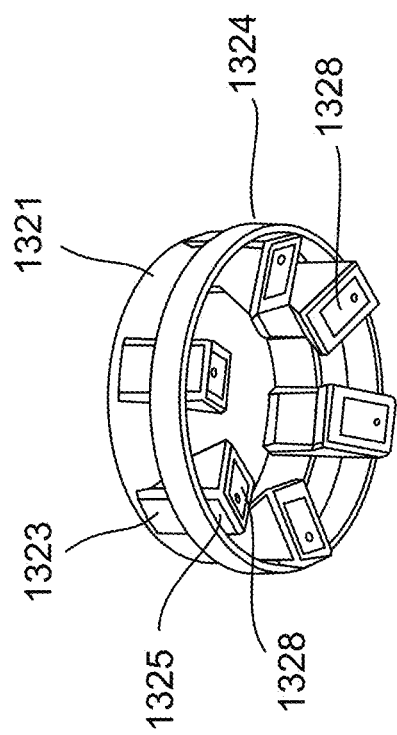

FIG. 13E is a top isometric view, FIG. 13F is a bottom isometric view, FIG. 13G is a bottom view, FIG. 13H is a top view and FIG. 13I is a side view.

In some embodiments one or more of the feet 1325 includes an optional plate 1326 to stiffen the feet 1325.

In some embodiments one or more of the feet 1325 includes an optional hole 1327 for connecting to an insertion tool, in some embodiments a connection tool as described elsewhere herein.

In some embodiments the spacing of the feet 1325 includes some spaces between the feet 1325 larger than other spaces between the feet 1325.

In some embodiments the larger spaces are, by way of a non-limiting example, at locations such as pointed out by arrows 1322.

In some embodiments the larger spaces are, by way of a non-limiting example, at "3 o'clock" and "9 o'clock".

In some embodiments the device includes markings to potentially guide a physician to a desired direction for placing the device upon a cervix.

In some embodiments the markings are, by way of a non-limiting example, at "12 o'clock" and "6 o'clock", at locations pointed out by arrows 1328.

The embodiment shown in FIGS. 13E-I optionally shares features with the embodiments shown and described with reference to FIGS. 2 and 5A-5C.

Reference is now made to FIGS. 13J-M, which are simplified illustrations of a device for retarding birth according to an example embodiment of the invention.

FIGS. 13J-M show a device which includes an upper ring 1331 for surrounding a uterine cervix; and an anchoring mechanism for anchoring the device on the cervix. The anchoring mechanism includes legs 1333, feet 1335 for pressing against a cervix and gripping the cervix, and a band 1334 for pressing the feet against the cervix.

Figure 13K:
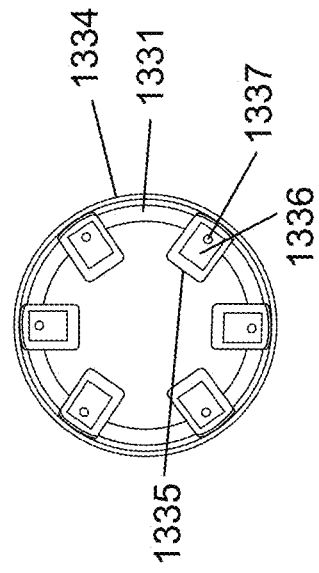
FIGS. 13J-M are simplified illustrations of a device for retarding birth according to an example embodiment of the invention.
Figure 13J:
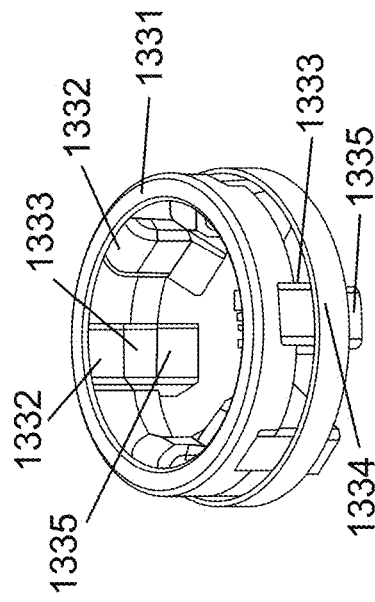
Figure 13L:
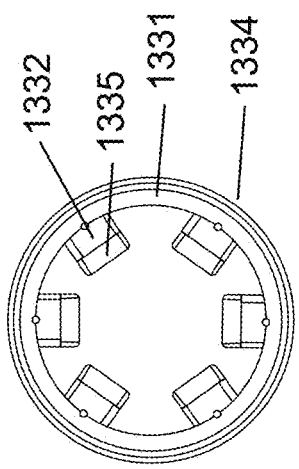
Figure 13M:
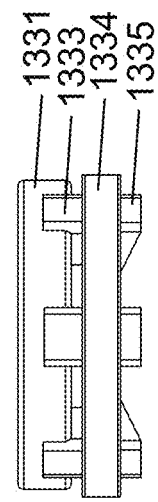

FIG. 13J is an isometric view, FIG. 13K is a bottom view, FIG. 13L is a top view and FIG. 13M is a side view.

In some embodiments one or more of the feet 1335 includes an optional plate 1336 to stiffen the feet 1335.

In some embodiments one or more of the feet 1335 includes an optional hole 1337 for connecting to an insertion tool, in some embodiments a connection tool as described elsewhere herein.

In some embodiments the upper ring 1331 is constructed to hold onto a cervix (not shown) at several sections of a circumference of the cervix, leaving other sections of the circumference of the cervix without pressing components, potentially easing blood flow in the cervix, potentially easing venous blood flow, which is near a surface of the cervix.

FIGS. 13J-M show a non-limiting example embodiment where protrusions 1332 optionally protrude into a lumen or space within the upper ring 1331. In some embodiments the number of protrusions may be 1, 2, 3, 4, 5, 6, 7, 8, 9, 10, or even greater.

In some embodiments the upper ring 1331 is not necessarily a ring, but rather termed an upper component 1331. The upper component 1331 defines an inner lumen for grasping and pressing onto certain sections of the cervix, and leaving other sections free, without pressure, potentially easing blood flow through at least the free sections.

In some embodiments the upper component 1331 includes projections such as protrusions 1332 for pressing onto the cervix.

In some embodiments the upper component 1331 is shaped as an oval (not shown), a triangle (not shown), a rectangle (not shown), a pentagon (not shown), a hexagon (not shown), some other shape with N straight sides (not shown), as a three-pointed star (not shown) or as an N-pointed star (not shown).

The embodiment shown in FIGS. 13J-M optionally shares features with the embodiments shown and described with reference to FIGS. 13E-I, 2 and 5A-5C.

Reference is now made to FIGS. 14A and 14B, which are simplified illustrations of a cervix grasping tool according to an example embodiment of the invention.

FIGS. 14A and 14B show a tool 1400 for grasping a cervix, the tool including two jaws 1411 1412 and a hinge 1410 connecting the two jaws 1411 1412.

FIG. 14A shows the tool 1400 in a jaws-closed position, and FIG. 14B shows the tool 1400 in a jaws-open position.

In some embodiments the grasping tool 1400 optionally includes additional hinges 1409a 1409b connected to extension handles 1406 1407, connected by a hinge 1402. The optional extension handles 1406 1407 potentially enable using the tool 1400 from further away from the cervix to be grasped. The optional extension handles 1406 1407 potentially enable using the tool 1400 from further away from a vagina through which the tool is inserted to grasp the cervix.

In some embodiments the tool 1400 optionally includes a scale 1408. The scale optionally indicates an extent to which the jaws 1411 1412 are open. In various embodiments the scale indicates the extent to which the jaws 1411 1412 are open in one or more of: indicating distance; indicating an angle; indicating a corresponding size of a suitable device for a device for retarding birth; indicating a corresponding size of one or more components of a suitable device for a device for retarding birth; and indicating an arbitrary number, potentially for use in selecting a suitable device for a device for retarding birth.

In some embodiments the tool 1400 optionally includes a spring for pushing open the extension handles 1406 1407, and a release lever 1404. In some embodiments the release lever 1404 optionally acts upon a tooth rack 1408, where pin 1405 is an optional end of travel stopper, releasing the extension handles 1406 1407 to separate, and the jaws 1411 1412 to open.

In some embodiments the lever 1404 is optionally slid forward or backward to operate the jaws 1411 1412.

Figure 14C:
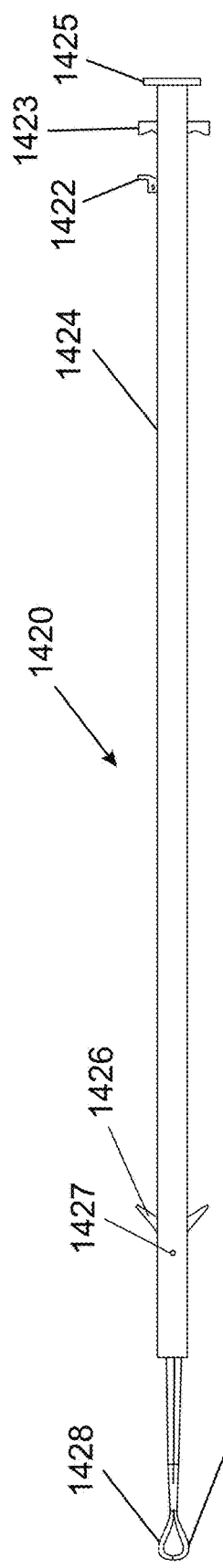
FIGS. 14C-E are simplified illustrations of a cervix grasping tool according to an example embodiment of the invention.
Figure 14D:
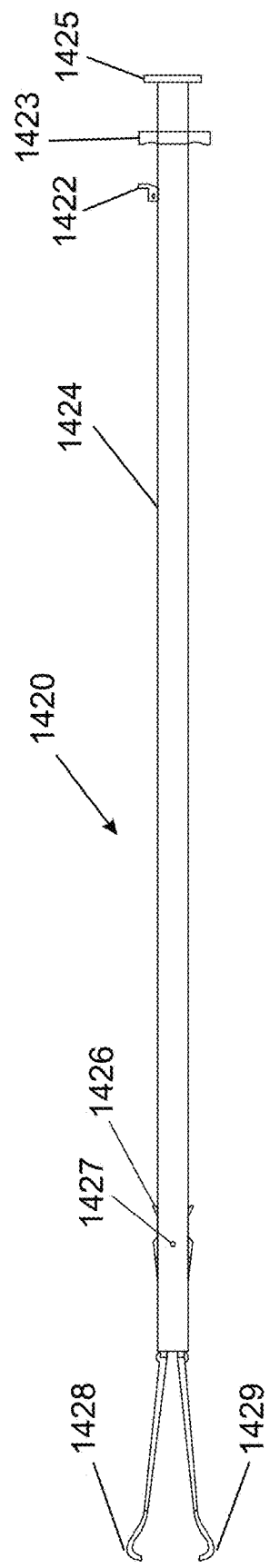
Figure 14E:
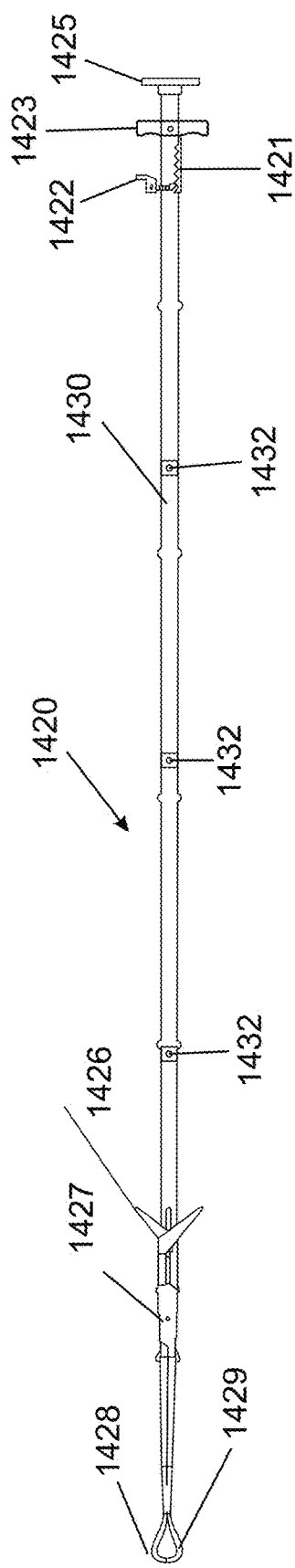

Reference is now made to FIGS. 14C-E, which are simplified illustrations of a cervix grasping tool according to an example embodiment of the invention.

FIGS. 14C and 14D show a tool 1420 for grasping a cervix, the tool including two jaws 1428 1429, a hinge 1427 connecting the two jaws 1428 1429, an extension tube 1424 and one or more controls 1422 1423 1425.

FIG. 14E shows the tool 1420 without the extension tube 1424, so as to expose inner parts of the tool 1420.

FIGS. 14C and 14E show the tool 1420 in a jaws-closed position, and FIG. 14D shows the tool 1420 in a jaws-open position.

A first control, optionally a button 1425 is optionally used to open and close the jaws 1428 1429, by optionally pushing a rod 1430 into the tube 1424 (open) or pulling the rod 1430 from the tube 1424 (close).

In some embodiments the tool 1420 optionally includes a spring (not shown) pushing the rod 1430 out of the tube 1424; the rod 1430 is optionally pushed against the spring in order to open the jaws 1428 1429, and the rod 1430 is released to close the jaws 1428 1429.

In some embodiments the tool 1420 optionally includes a handle 1423 for use when pushing the button 1425.

In some embodiments the tool 1420 optionally includes a latch 1422, optionally used against a ratchet 1421, for locking and/or releasing the rod 1430 to move along the tube 1424, and open and/or close the jaws 1428 1429.

FIG. 14C shows a non-limiting example of a rod 1430 with several segments connected by hinges 1432. In some embodiments, the tool may be bent to enter a body via the vagina and grasp a cervix. In some embodiments, the tube 1424 may be flexible.

Reference is now made to FIGS. 15A-D, which are simplified illustrations of an insertion tool for inserting a device for retarding birth according to an example embodiment of the invention.

FIGS. 15A-D show an insertion tool 1500 for inserting a device 1502 for retarding birth.

Figure 15A:
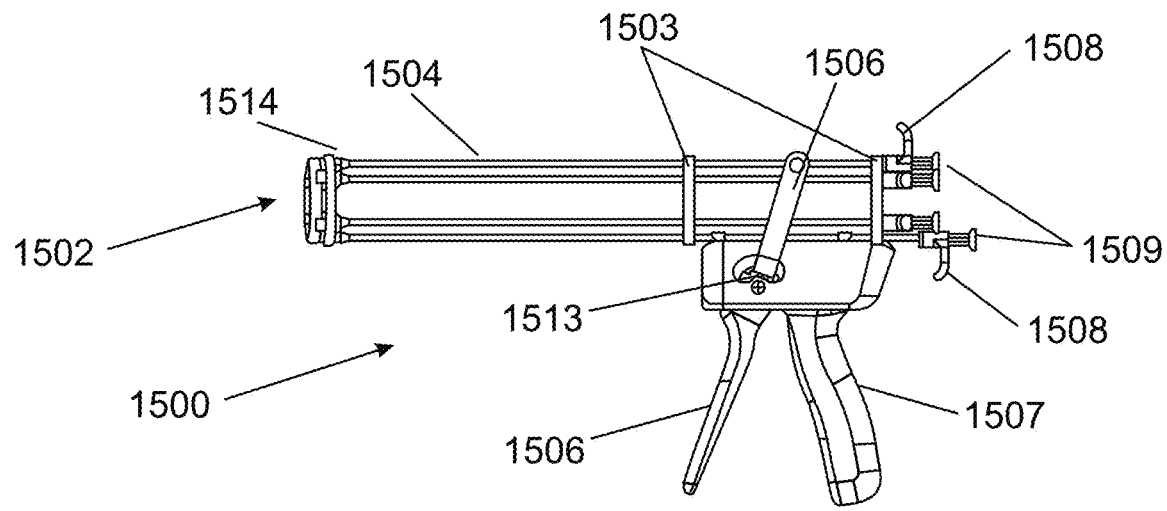
FIGS. 15A-D are simplified illustrations of an insertion tool for inserting a device for retarding birth according to an example embodiment of the invention.
Figure 15B:
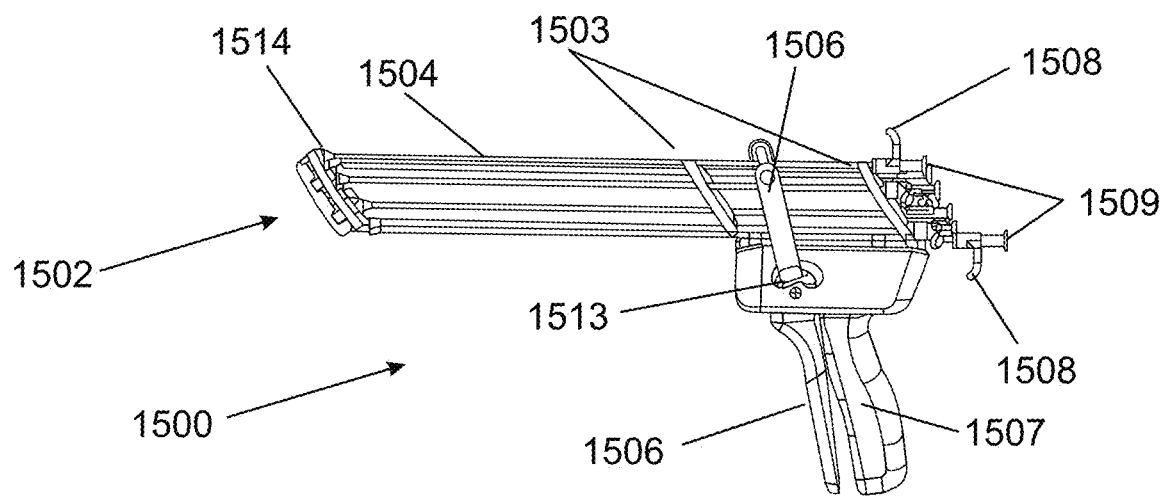

FIGS. 15A and 15B show the device 1502 for retarding birth mounted onto a distal end of the insertion tool 1500.

The insertion tool 1500 includes rods 1504 and rings 1503, to which the rods 1504 are attached, forming a shape of a lumen surrounded by the rods 1504.

The device 1502 may optionally be attached to a distal end of the rods 1504.

In some embodiments, the device 1502 is optionally inserted into a vagina (not shown) when attached to the distal end of the insertion tool 1500, and optionally maneuvered to surround and grip a cervix (not shown).

The shape of the lumen surrounded by the rods 1504 is optionally changed, by moving some of the rods 1504 longitudinally relative to the other rods 1504, for example as shown in FIG. 15B. In such a case the distance between the rods 1504 is optionally reduced, optionally forming a narrower lumen, at least across one dimension of a cross section of the lumen. In such a case the insertion tool, with or without the device 1502 attached, can potentially pass more easily through a vagina and/or a speculum (not shown), and/or potentially less distension of the vagina is needed in order to insert the device 1502 using the insertion tool 1500.

In some embodiments shape of the lumen surrounded by the rods 1504 is optionally changed from a round shape to an oval shape.

In some embodiments shape of the lumen surrounded by the rods 1504 is optionally changed from an oval shape to another oval shape, having a different length of a minor axis of the oval or a different length of a major axis of the oval.

In some embodiments, the insertion tool includes one or more of:
- cups 1514 or pins for pushing the device 1502 from the distal end of the rods 1504;
- mechanisms at a proximal end of the rods 1504, for optionally detaching the device 1502 from the distal ends of the rods 1504. FIGS. 15A and 15B show the mechanism for detaching the device 1502 including a handle 1508 and/or a button 1509. In some embodiments the device 1502 is optionally detached from the distal end of a rod 1504 by pulling on the handle 1508 at the proximal end of that rod 1504;

In some embodiments an optional button 1509 enables fine tuning of a position of the device in the fornix. For example, by pushing on each of the buttons 1509 buttons separately, the rods push the device each at a different location, potentially enabling placement fully surrounding the cervix in the fornix;
- an optional grip 1507 for the insertion tool 1500; and
- an optional lever 1506 with a hinge 1513 which, when squeezed, moves the rods 1504 longitudinally and changes a cross-sectional shape of the lumen formed by the rods 1504.

Figure 15C:
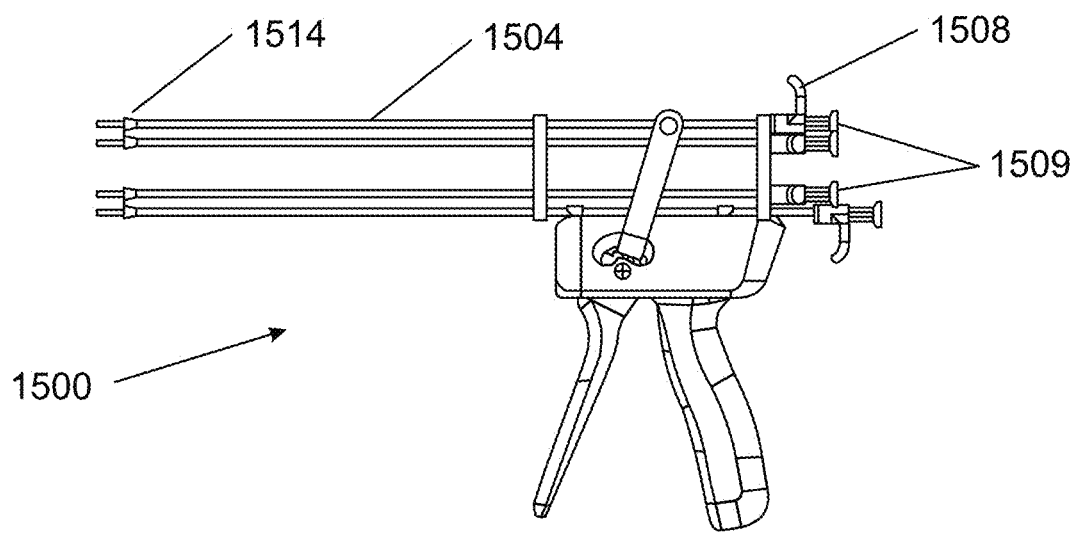

FIG. 15C shows that when the button 1508 is optionally pulled backward, the cup 1514 or pin is optionally pulled back along the rods 1504, freeing a distal end of the rods for attaching the device 1502 (not shown in FIG. 15C).

Figure 15D:
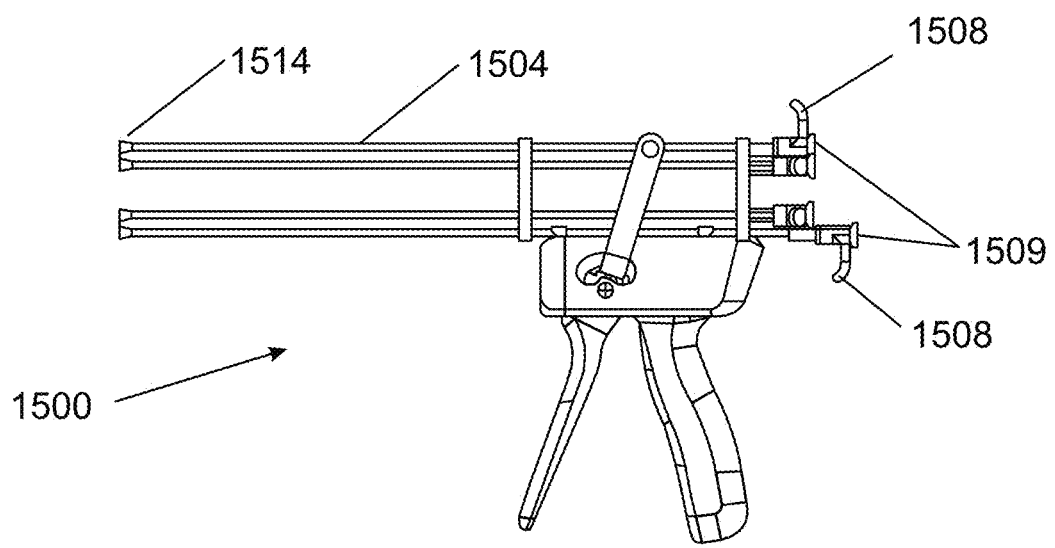

FIG. 15D shows that when the handle 1508 is optionally slid forward along the rods 1504, the cup 1514 or pin optionally pushed the device 1502 (not shown in FIG. 15D) off a distal end of the rods 1504.

Figure 16A:
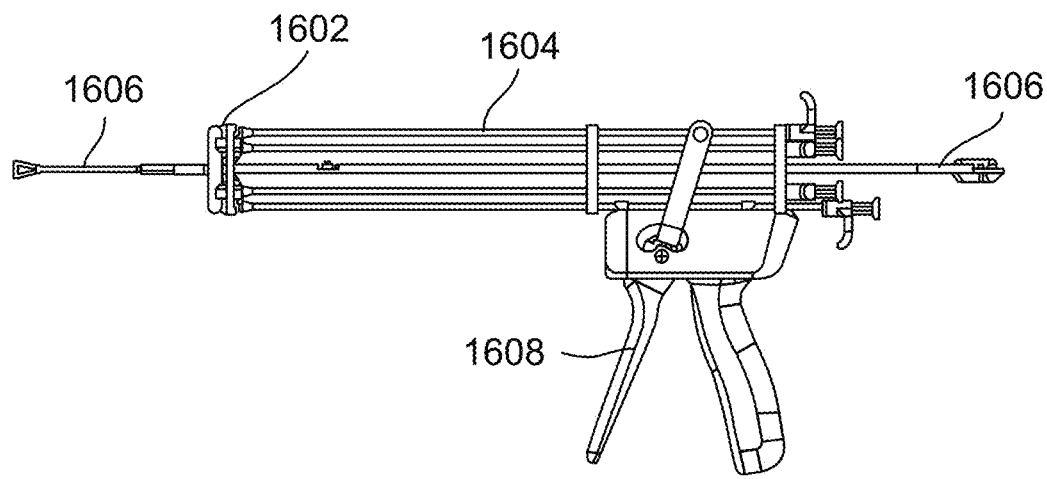
FIGS. 16A and 16B are simplified illustrations of the insertion tool of FIGS. 15A and 15B ready for inserting a device for retarding birth and a grasping tool for grasping a cervix, according to an example embodiment of the invention.
Figure 16B:
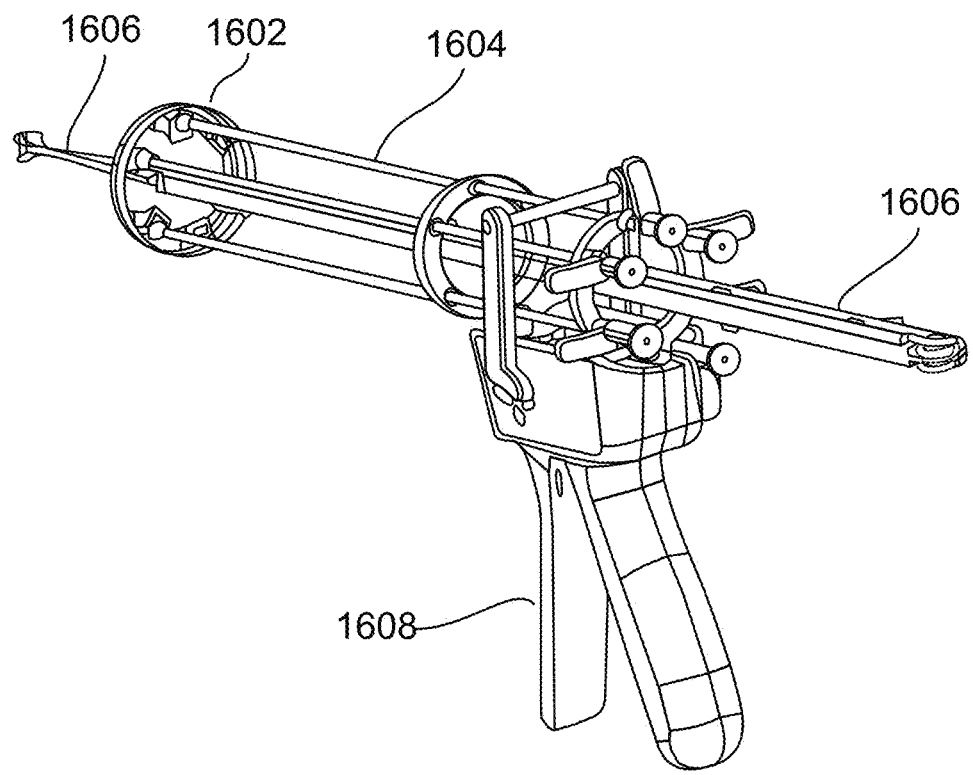

Reference is now made to FIGS. 16A and 16B, which are simplified illustrations of the insertion tool of FIGS. 15A and 15B ready for inserting a device for retarding birth and a grasping tool for grasping a cervix, according to an example embodiment of the invention.

FIG. 16A is a cross-sectional side view, and FIG. 16B is an isometric view.

Figure 16C:
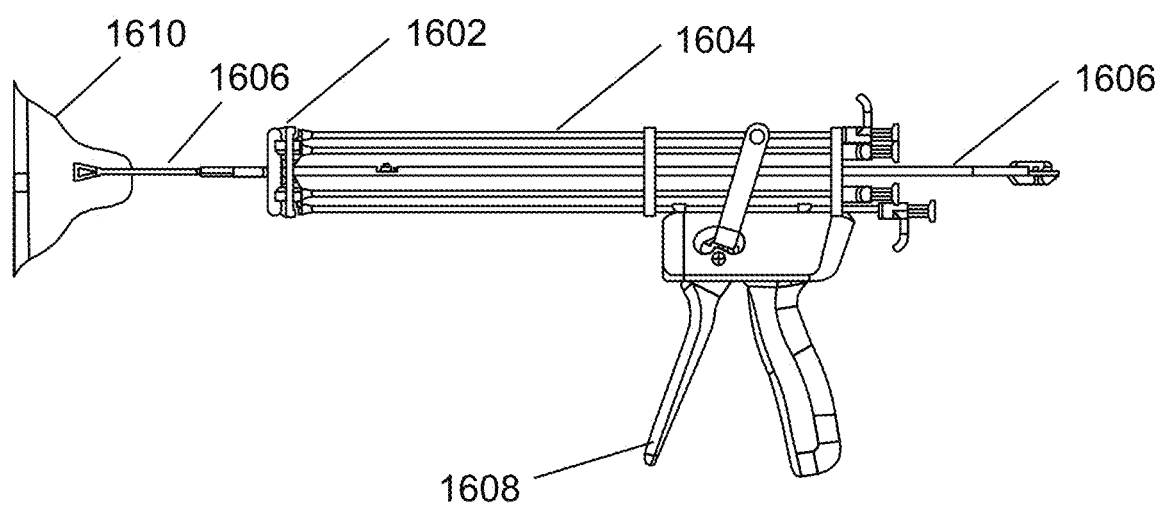
FIG. 16C is a simplified illustration of the insertion tool of FIGS. 15A and 15B inserting a device for retarding birth and the grasping tool of FIG. 16A grasping a cervix according to an example embodiment of the invention.

Reference is additionally made to FIG. 16C, which is a simplified illustration of the insertion tool of FIGS. 15A and 15B inserting a device for retarding birth and the grasping tool of FIG. 16A grasping a cervix according to an example embodiment of the invention.

FIGS. 16A-C show an insertion tool 1604, to which is attached a device 1602 for retarding birth, and through which passes a grasping tool 1606 such as, by way of a non-limiting example, the grasping tool 1400 of FIGS. 14A and 14B or the grasping tool 1420 of FIGS. 14C and 14D.

FIGS. 16A and 16B shows the insertion tool 1604, the device 1602 and the grasping tool 1606 assembled as they would be, by way of a non-limiting example, prior to inserting into a vagina.

In some embodiments the assembly of the insertion tool 1604, the device 1602 and the grasping tool 1606 is optionally inserted as-is into a vagina.

In some embodiments the assembly of the insertion tool 1604, the device 1602 and the grasping tool 1606 is optionally inserted through a speculum.

In some embodiments a lever 1608 of the insertion tool 1604 is optionally squeezed, optionally by operating a lever 1608, and a cross sectional area of the insertion tool 1604 is optionally decreased before inserting the assembly of the insertion tool 1604, the device 1602 and the grasping tool 1606 into a vagina.

FIG. 16C shows the insertion tool 1604, the device 1602 and the grasping tool 1606 as they would be within a vagina, with the insertion tool 1604 in an un-compressed state, and the grasping tool grasping a cervix 1610.

Figure 16D:
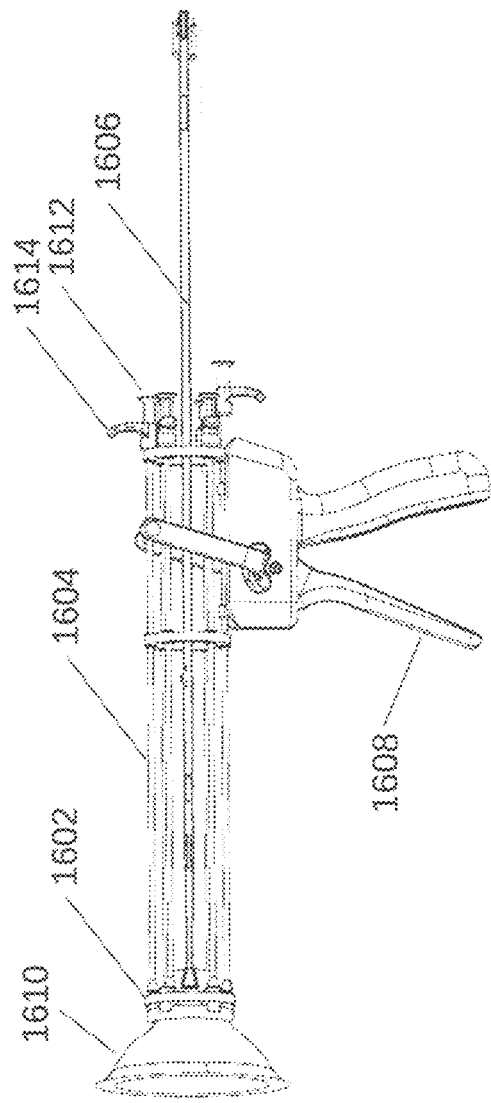
FIG. 16D is a simplified illustration of the insertion tool of FIGS. 16A and 16B with a grasping tool pulling a cervix into a device for retarding birth according to an example embodiment of the invention.

Reference is now made to FIG. 16D, which is a simplified illustration of the insertion tool of FIGS. 16A-C with a grasping tool pulling a cervix into a device for retarding birth according to an example embodiment of the invention.

FIG. 16D shows the grasping tool 1606 grasping the cervix 1610, and optionally pulling the cervix 1610, optionally positioning the device 1602 for retarding birth high upon the cervix 1610. FIG. 16D shows the grasping tool 1606 pulled back relative to the insertion tool 1604.

After positioning the device 1602 for retarding birth on the cervix 1610, a mechanism for detaching the device 1602 from the insertion tool 1604 is optionally operated, to detach the device 1602.

In some embodiments operating the mechanism for detaching the device 1602 optionally includes pressing on one or more button(s) 1612.

In some embodiments operating the mechanism for detaching the device 1602 optionally includes operating a handle 1614.

In some embodiments there are six rods 1504 in the insertion tool 1500. In some embodiments, the rods at 12 o'clock and at 6 o'clock are optionally attached to the optional grip 1507 and are not designed be pushed forward. The other 4 rods can be pushed forward. Such a configuration potentially enables positioning the device 1502 accurately and high up around the cervix, in a way which potentially locates an upper ring of the device 1502 at the fornix, optionally touching tissue all around the fornix.

Figure 16E:
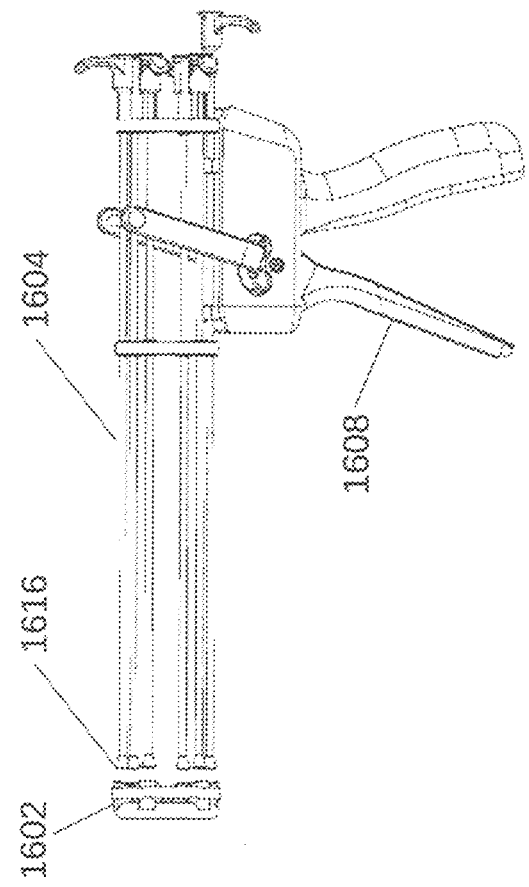
FIG. 16E is a simplified illustration of the insertion tool of FIGS. 16A and 16B detached from a device for retarding birth according to an example embodiment of the invention.

Reference is now made to FIG. 16E, which is a simplified illustration of the insertion tool of FIGS. 16A-C detached from a device for retarding birth according to an example embodiment of the invention.

FIG. 16E shows distal ends 1616 of the insertion tool 1604 detached from the device 1602.

FIG. 16E does not show the cervix grasping tool 1606. In some embodiments the cervix grasping tool 1606 is optionally withdrawn from the insertion tool 1604 before the device 1602 is detached from the insertion tool 1604. In some embodiments the cervix grasping tool 1606 is optionally withdrawn from the insertion tool 1604 after the device 1602 is detached from the insertion tool 1604.

In some embodiments the cervix grasping tool 1606 is withdrawn from the vagina before the insertion tool 1604 is detached from the device 1602.

In some embodiments the cervix grasping tool 1606 is withdrawn from the vagina before the insertion tool 1604 is withdrawn from the vagina, and after the insertion tool 1604 is detached from the device 1602.

In some embodiments the cervix grasping tool 1606 the insertion tool 1604 are withdrawn together from the vagina.

Figure 16F:
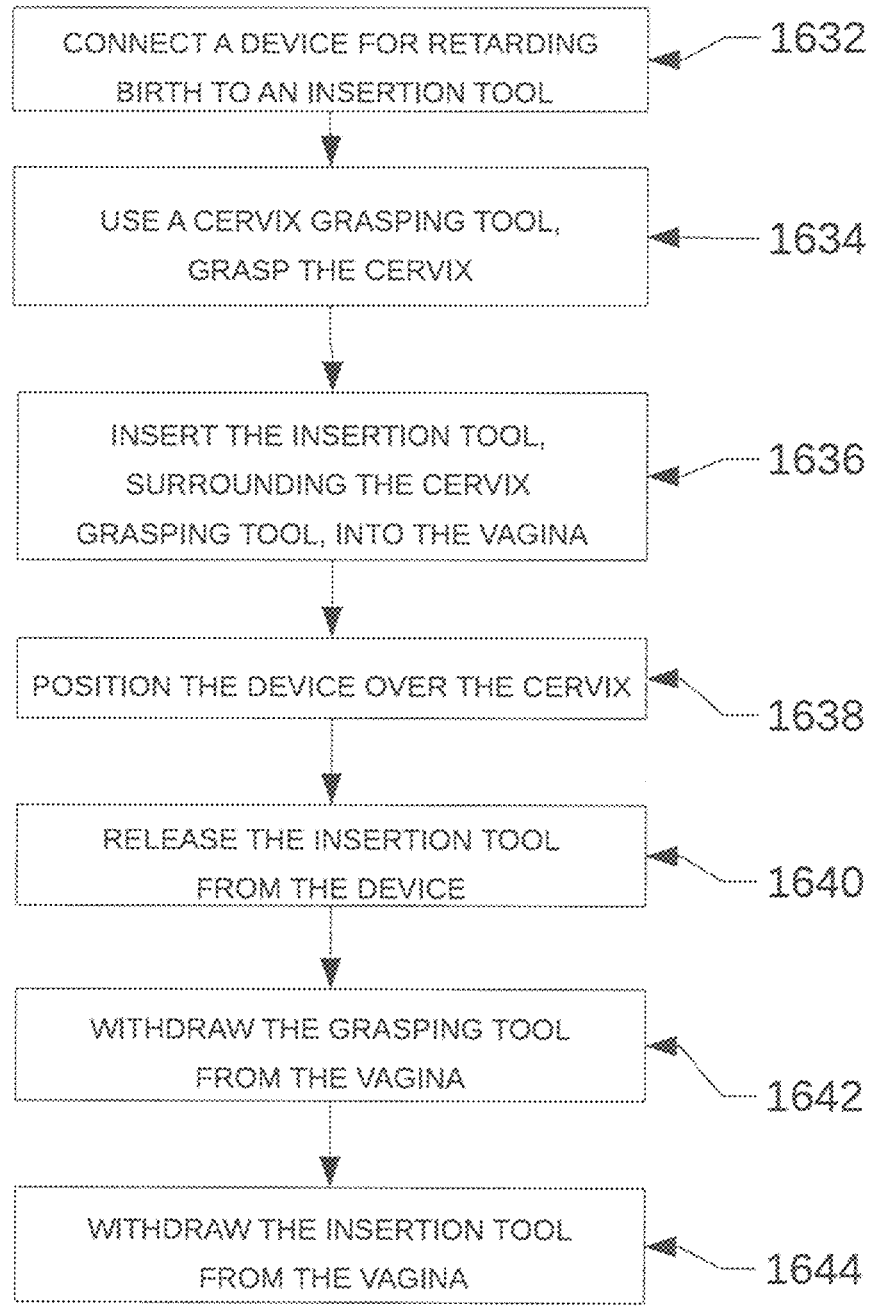
FIG. 16F is a simplified flow chart illustration of a method for placing a device for retarding birth on a cervix, according to an example embodiment of the invention.

Reference is now made to FIG. 16F, which is a simplified flow chart illustration of a method for placing a device for retarding birth on a cervix, according to an example embodiment of the invention.

The cervix may sometimes be in an anterior, a posterior, a left or a right angle.

In some embodiments a grasping tool is optionally used to grasp the cervix and position the cervix centrally in order to enable good placement of the device.

In some embodiments, an insertion tool may optionally include a scope that allows visualizing of the insertion process on a screen, at a proximal end of the insertion tool and/or on an outside screen. Use of a screen potentially enables good visualization of the cervix and the insertion process.

In some embodiments a method for placing a device for retarding birth on a cervix optionally includes:
- connect a device for retarding birth to an insertion tool (1632);
- using a cervix grasping tool, grasp the cervix (1634).
- insert the insertion tool, surrounding the cervix grasping tool, into the vagina (1636);
- position the device over the cervix (1638);
- release the insertion tool from the device (1640);
- withdraw the grasping tool from the vagina (1642); and
- withdraw the insertion tool from the vagina (1644).

In some embodiments, before connecting the device to the insertion tool, optionally insert the cervix grasping tool into the vagina, and optionally measure a diameter of the cervix.

In some embodiments, optionally choose a correct size of a device for retarding birth, optionally based on the measurement.

In some embodiments, optionally connect the device to the insertion tool with optional markings at 12 o'clock and at 6 o'clock.

In some embodiments, perform the grasping of the cervix by the cervix grasping tool optionally at two sides of the cervix, optionally at 3 o'clock and 9 o'clock.

In some embodiments, the grasping of the cervix is optionally performed after inserting the insertion tool surrounding the cervix grasping tool into the vagina.

In some embodiments the insertion of the insertion tool and/or the grasping tool is optionally done through a speculum.

In some embodiments, after positioning the device over the cervix, optionally adjust location of the device by pressing ends of the rods. Optionally locate the device at the fornix.

In some embodiments the withdrawing of the grasping tool from the vagina is performed together with withdrawing the insertion tool from the vagina.

In some embodiments the withdrawing of the grasping tool from the vagina is performed before withdrawing the insertion tool from the vagina.

In some embodiments the withdrawing of the insertion tool from the vagina is performed before withdrawing the grasping tool from the vagina.

In some embodiments, such as for example shown in FIG. 16A-E, there are six rods 1504 in the insertion tool 1500. In some embodiments, the rods at 12 o'clock and at 6 o'clock are optionally attached to the optional grip 1507 and are not designed be pushed forward. The other 4 rods can be pushed forward. Such a configuration potentially enables positioning the device 1502 accurately and high up around the cervix, in a way which potentially locates an upper ring of the device 1502 at the fornix, optionally touching tissue all around the fornix.

Reference is now made to FIGS. 17A-C, which are simplified illustrations of a device for retarding birth placed around a uterine cervix according to an example embodiment of the invention.

FIGS. 17A-C show a device for retarding birth placed around a cervix 1710, and also shows vagina walls 1712. The cervix 1710 is optionally in a state corresponding to pregnancy, and not yet to delivery or birth.

FIG. 17A is a side cross-sectional view, FIG. 17B is a bottom isometric view, and FIG. 17C is a bottom view.

FIGS. 17A-C show a device for retarding birth, including an upper ring 1702 placed around the cervix 1710, legs 1704 and feet 1706 surrounded by a band 1708. The band 1708 presses upon the legs 1704, pressing the feet 1706 upon the cervix 1710.

The device for retarding birth potentially presses upon the cervix 1710, and potentially helps to keep it supporting a fetus and potentially delays funneling and/or dilatation of the cervix and/or pre-term birth and/or pre-term delivery.

However, delivery or birth may start, and in some embodiments the device for retarding birth is optionally configured to support the cervix up to a specific point, and then give in, release the cervix and allow birth to happen. In some embodiments the "giving in" is by the device inverting, the upper ring releasing the cervix and/or the anchors releasing the cervix.

Figure 18B:
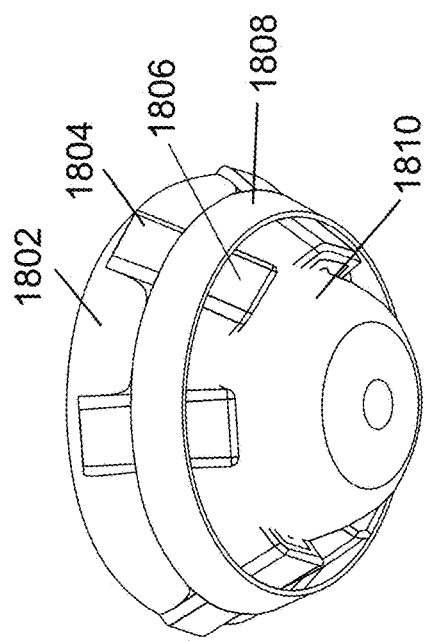
FIGS. 18A-C are simplified illustrations of a device for retarding birth placed around a uterine cervix, with the uterine cervix under pressure, according to an example embodiment of the invention.
Figure 18C:
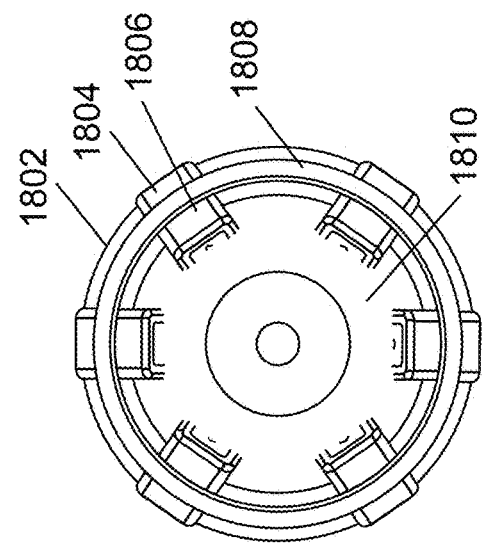
Figure 18A:
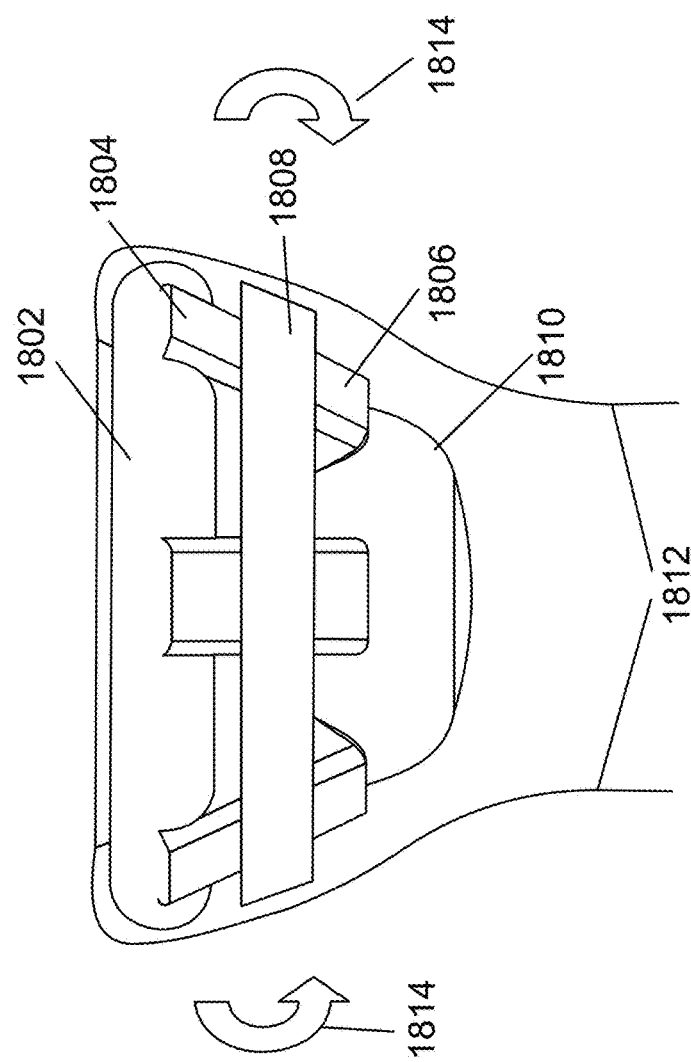

Reference is now made to FIGS. 18A-C, which are simplified illustrations of a device for retarding birth placed around a uterine cervix, with the uterine cervix under pressure, according to an example embodiment of the invention.

FIGS. 18A-C show a device for retarding birth placed around a cervix 1810, with the cervix under pressure, and also shows vagina walls 1812. The cervix 1810 is optionally in a state of pressure from above, and the device not yet released from the cervix 1810.

FIG. 18A is a side cross-sectional view, FIG. 18B is a bottom isometric view, and FIG. 18C is a bottom view.

FIGS. 18A-C show a device for retarding birth, including an upper ring 1802 placed around the cervix 1810, legs 1804 and feet 1806 surrounded by a band 1808. The band 1808 presses upon the legs 1804, pressing the feet 1806 upon the cervix 1810.

However, the cervix 1810 is in a more-distended state than the cervix 1710 shown in FIGS. 17A-17C. The upper ring 1802 is more distended, a top of the legs 1804 is extended sideways, and the feet are further in toward a center of a lumen defined by the shape of the device.

In some embodiments, under additional pressure from the cervix 1810, the device inverts, the upper ring 1802 optionally flips over the band 1808 and the feet of the legs 1806, in a direction pointed out by arrow 1814.

It is noted that pressure may come from the uterus. This pressure may cause dilatation of the internal os of the cervix and such pressure potentially affects the upper ring of the device.

Figure 18E:
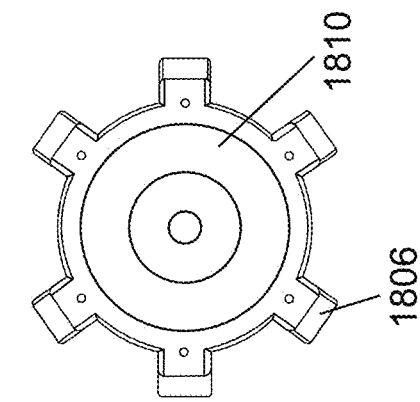
FIGS. 18D and 18E are simplified illustrations of a device for retarding birth following inversion on a uterine cervix, according to an example embodiment of the invention.
Figure 18D:
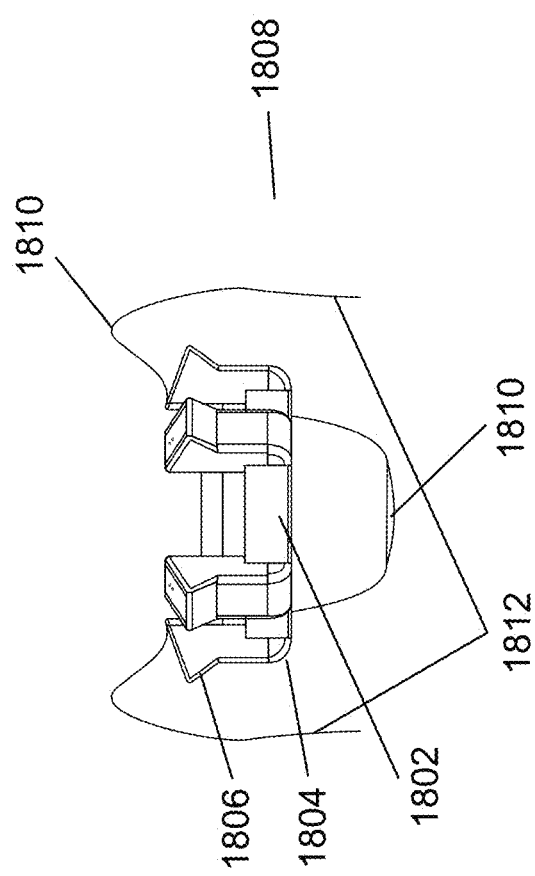

Reference is now made to FIGS. 18D and 18E, which are simplified illustrations of a device for retarding birth following inversion on a uterine cervix, according to an example embodiment of the invention.

FIG. 18D is a side cross-sectional view and FIG. 18E is a bottom view.

FIGS. 18D and 18E show a device for retarding birth, including an upper ring 1802 placed around the cervix 1810, legs 1804 and feet 1806, and a band 1808.

The device has inverted, and a side of the feet 1806 which pressed against the cervix 1810, for example in FIG. 18A, now points outward, not against the cervix.

In some embodiments, the feet 1806 are not any more anchoring the device on the cervix.

In some embodiments, the pressure of the cervix upon the device, which was enough to invert the device, is enough to slip the device off the cervix.

Figure 19:
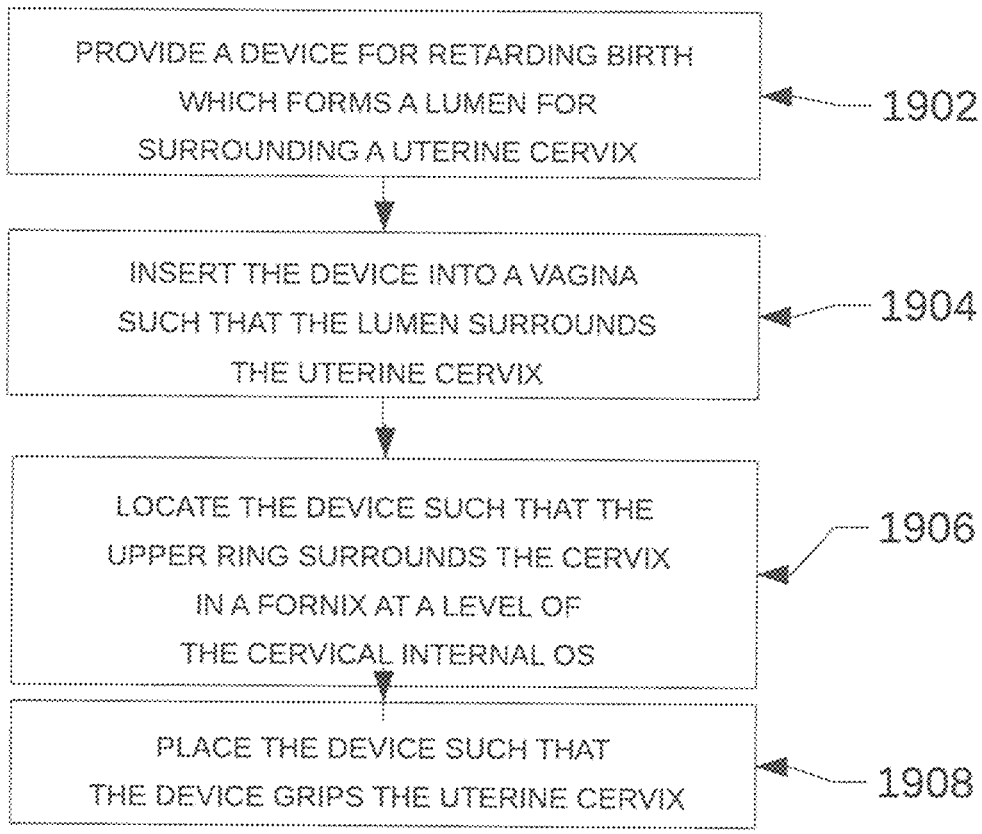
FIG. 19 is a simplified method for retarding birth according to an example embodiment of the invention.

Reference is now made to FIG. 19, which is a simplified method for retarding birth according to an example embodiment of the invention.

The method of FIG. 19 includes:
providing a device for retarding birth which forms a lumen for surrounding a uterine cervix (1902);
inserting the device into a vagina such that the lumen surrounds the uterine cervix (1904);
locating the device such that the upper ring surrounds the cervix in a fornix at a level of the cervical internal os (1906); and
placing the device such that the device grips the uterine cervix (1908).

Figure 20:
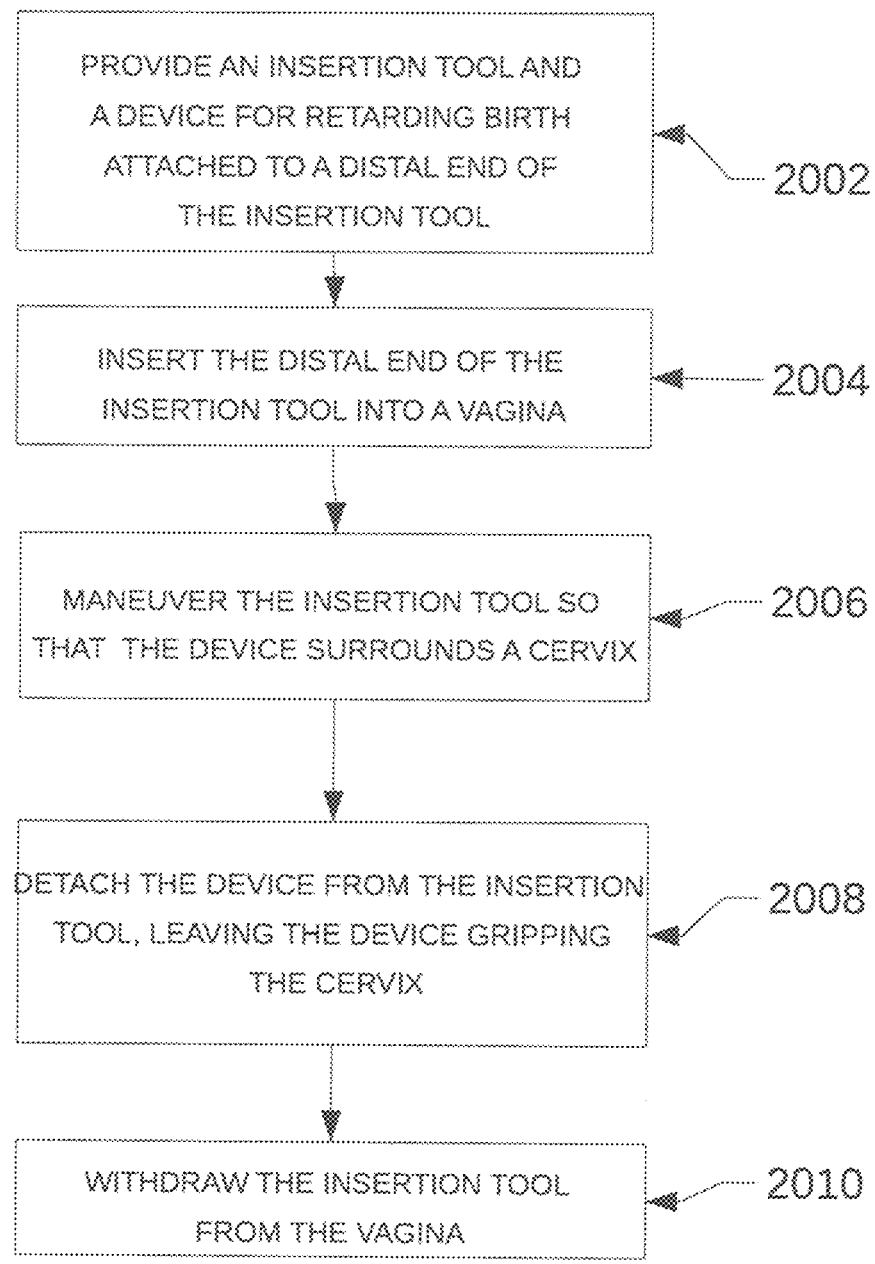
FIG. 20 is a simplified method for retarding birth according to an example embodiment of the invention.

Reference is now made to FIG. 20, which is a simplified method for retarding birth according to an example embodiment of the invention.

The method of FIG. 20 includes:
providing an insertion tool and a device for retarding birth attached to a distal end of the insertion tool (2002);
inserting the distal end of the insertion tool into a vagina (2004);
maneuvering the insertion tool so that the device surrounds a cervix (2006);
detaching the device from the insertion tool, leaving the device gripping the cervix (2008); and
withdrawing the insertion tool from the vagina (2010).

In some embodiments the locating of the device such that the upper ring surrounds the cervix in a fornix at a level of the cervical internal os means locating the device such that the upper ring surrounds the cervix in a fornix within approximately 0-10, 15, 20, 25, 30, 40 and 50 millimeters, for example 5 millimeters, from the level of the cervical internal os.

As used herein the term "about" refers to ±10%.

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example or exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the engineering, chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

What is claimed is:

1. A method for retarding birth comprising:
providing an insertion tool and a device for retarding birth attached to a distal end of the insertion tool;
inserting the distal end of the insertion tool into a vagina;
maneuvering the insertion tool so that the device surrounds a cervix;
detaching the device from the insertion tool, leaving the device gripping the cervix; and
withdrawing the insertion tool from the vagina,
wherein the insertion tool comprises:
a plurality of rods configured to be attached to the device, each rod comprising
a distal end shaped to attach to the device for retarding birth,
wherein said inserting and/or maneuvering comprise manipulating at least one of said rods to move axially relative to at least another of said rods, thereby changing the layout of said device for retarding birth
wherein the device for retarding birth is configured to form a lumen for surrounding a uterine cervix, the device comprising:
an upper ring for surrounding the uterine cervix; and
an anchor for anchoring the device on the cervix,
wherein the anchor comprises a plurality of legs attached at one end to the upper ring, the legs comprising another lower end configured to anchor against the cervix; and
wherein at least two of the plurality of legs of the device for retarding birth comprise a hole for inserting the distal end of the rods of the insertion tool, thereby attaching the insertion tool to the device for retarding birth.

2. The method according to claim 1, wherein the providing the insertion tool and the device further comprises providing a grasping tool inserted through a lumen of the insertion tool.

3. The method according to claim 2, and further comprising grasping the cervix with the grasping tool before the inserting of the distal end of the insertion tool into the vagina.

4. The method according to claim 3, and further comprising pulling the cervix with the grasping tool prior to the detaching of the device from the insertion tool.

5. The method according to claim 1, wherein the rods are flexibly attached to at least some of the plurality of legs of the device for retarding birth, enabling a cross section of a longitudinal lumen of the insertion tool to expand and contract.

6. The method according to claim 1, wherein the legs of the device for retarding birth are flexible, enabling a cross section of the lumen to expand and contract.

7. The method according to claim 5, comprising contracting the cross section of the longitudinal lumen before inserting the distal end of the insertion tool into a vagina.

8. The method according to claim 1 and further comprising attaching the device for retarding birth to the cervix using an adhesive material.

9. The method of claim 1, wherein said maneuvering comprises moving the rods to change an angle of attachment of the rods to the device for retarding birth.

10. The method according to claim 1, wherein said insertion tool comprises a mechanism at a proximal end for causing release of at least part of said device from the distal ends of the rods.

11. The method according to claim 1, wherein said detaching comprises applying a distally directed axial force by at least one of said rods.

12. The method according to claim 1, wherein said manipulating changes a shape of said device to be oval.

13. The method according to claim 1, wherein said plurality of rods comprises more than two rods.

14. The method according to claim 1, wherein said rods are held in a circumferential relationship by a ring through which the rods pass.

15. The method according to claim 1, wherein said detaching comprises releasing said device for retarding birth to elastically deform and engage said cervix.

16. The method according to claim 1, wherein said inserting comprises modifying the relative positions of said rods to assist in insertion through a speculum.

17. The method according to claim 1, comprising fine tuning of a position of the device for retarding on the cervix by selective manipulation of said rods.

18. The method according to claim 1, wherein the device for retarding comprises a plurality of anchoring legs and wherein detaching comprises selectively releasing at least one of said legs before releasing another of said legs.

19. An insertion tool for inserting a device for retarding birth, the device forming a device lumen for surrounding a uterine cervix, the tool comprising:
a plurality of rods attached to a ring, forming a longitudinal tool lumen, each rod comprising:
a connector for attaching to the device for retarding birth at a distal end of the rod; and
a mechanism at a proximal end of the rod, for detaching the device for retarding birth at the distal end of the rod,
a device for retarding birth by being placed on a-cervix attached to said rods and capable of being detached from the rods, comprising:
an upper ring for surrounding the uterine cervix; and
an anchor for anchoring the device on the cervix,
wherein the anchor comprises a plurality of legs attached at one end to the upper ring, the legs comprising another lower end configured to anchor against the cervix;
wherein the rods of the insertion tool are configured so that at least one rod can move axially relative to at least another rod while said device for retarding birth is mounted thereon, thereby changing the layout of said device for retarding birth during maneuvering of the insertion tool;
wherein at least two of the plurality of legs of the device for retarding birth comprise a hole for inserting the distal end of the rods of the insertion tool, thereby attaching the insertion tool to the device for retarding birth; and
wherein upon detachment of the device for retarding birth from the rods, the device remains gripping the cervix.

20. The insertion tool according to claim 19, wherein the ring is flexible, enabling a cross section of the longitudinal tool lumen to expand and contract.

21. The insertion tool according to claim 19 wherein moving the rods, moves one or more rods longitudinally relative to one or more other rods, thereby forming an oval cross section of the tool lumen.

22. The insertion tool according to claim 19 and further comprising a lever for moving the rods closer to each other, thereby shrinking a cross section of the tool lumen.

23. The insertion tool according to claim 22 wherein the lever for moving the rods closer to each other, moves one or more rods longitudinally relative to one or more other rods, thereby forming an oval cross section of the tool lumen.

24. The insertion tool according to claim 19 wherein the rods are enabled to move apart from each other thereby expanding a cross section of the tool lumen and expanding an attached device for retarding birth.

25. The insertion tool according to claim 19 wherein the rods comprise channels along the rods for dispensing adhesive material to a device for retarding birth.

26. A method for retarding birth comprising:
providing an insertion tool and a device for retarding birth attached to a distal end of the insertion tool;
inserting the distal end of the insertion tool into a vagina;
maneuvering the insertion tool so that the device surrounds a cervix;
detaching the device from the insertion tool, leaving the device gripping the cervix; and
withdrawing the insertion tool from the vagina,
wherein the insertion tool comprises:
a plurality of rods configured to be attached to the device, each rod comprising a distal end shaped to attach to the device for retarding birth,
wherein said inserting and/or maneuvering comprise manipulating at least one of said rods to move axially relative to at least another of said rods, thereby changing the layout of said device for retarding birth;
wherein the rods are flexibly attached to at least some of the plurality of legs of the device for retarding birth, enabling a cross section of a longitudinal lumen of the insertion tool to expand and contract;
wherein the device for retarding birth is configured to form a lumen for surrounding a uterine cervix, the device comprising:
an upper ring for surrounding the uterine cervix; and
an anchor for anchoring the device on the cervix,
wherein the anchor comprises a plurality of legs attached at one end to the upper ring, the legs comprising another lower end configured to anchor against the cervix; and
further comprising contracting the cross section of the longitudinal lumen before inserting the distal end of the insertion tool into a vagina.

* * * * *